(12) United States Patent
Mevissen et al.

(10) Patent No.: US 9,587,265 B2
(45) Date of Patent: Mar. 7, 2017

(54) UBIQUITIN CHAIN ANALYSIS

(71) Applicant: Medical Research Council, Swindon (GB)

(72) Inventors: Tycho E. T. Mevissen, Cambridge (GB); Manuela K. Hospenthal, Cambridge (GB); David Komander, Cambridge (GB)

(73) Assignee: Medical Research Council, Swindon (GB)

( * ) Notice: Subject to any disclaimer, the term of this patent is extended or adjusted under 35 U.S.C. 154(b) by 0 days.

(21) Appl. No.: 14/346,284

(22) PCT Filed: Sep. 24, 2012

(86) PCT No.: PCT/EP2012/003987
§ 371 (c)(1),
(2) Date: Mar. 20, 2014

(87) PCT Pub. No.: WO2013/041241
PCT Pub. Date: Mar. 28, 2013

(65) Prior Publication Data
US 2014/0220591 A1    Aug. 7, 2014

(30) Foreign Application Priority Data

Sep. 23, 2011  (GB) .................................. 1116526.3
Jun. 26, 2012  (GB) .................................. 1211446.8

(51) Int. Cl.
*C12Q 1/37* (2006.01)
*C12N 9/48* (2006.01)
*G01N 33/68* (2006.01)

(52) U.S. Cl.
CPC ............... *C12Q 1/37* (2013.01); *C12N 9/485* (2013.01); *G01N 33/6842* (2013.01); *G01N 2440/36* (2013.01)

(58) Field of Classification Search
None
See application file for complete search history.

(56) References Cited

U.S. PATENT DOCUMENTS

2003/0108947 A1   6/2003   Issakani et al.
2007/0218069 A1   9/2007   Gordon et al.

FOREIGN PATENT DOCUMENTS

EP      1 808 493 A2    7/2007

OTHER PUBLICATIONS

Wang et al., "Evidence for Bidentate Substrate Binding as the Basis for the K48 Linkage Specificity of Otubain 1", J. Mol. Biol. (2009) 386, 1011-1023. doi:10.1016/j.jmb.2008.12.085.*
Komander et al., "Molecular discrimination of structurally equivalent Lys-63-linked and linear polyubiquitin chains", EMBO Reports, 2009, 10(5):466-473.*
Komander et al., "Breaking the chains: structure and function of the deubiquitinases", Nature Reviews: Molecular Cell Biology, Aug. 2009, 10:550-563.*
Ye et al., "Polyubiquitin binding and cross-reactivity in the USP domain deubiquitinase USP21", EMBO Reports, 2011, 12(4):350-357. Published on-line Mar. 2011. doi:10.1038/embor.2011.17.*
Mirzael, et al., "Characterizing the connectivity of poly-ubiquitin chains by selected reaction monitoring mass spectrometry", NIH-PA Author Manuscript, PMC, Mar. 15, 2011, p. 1-23.
Nishikawa, et al., "Mass Spectrometry and Mutational Analysis Reveal Lys-6-Linked Polyubiquitin Chains Catalyzed by BRCA1-BARD1 Ubiquitin Ligase", J. Biol. Chem., 279(6):3916-24 (2004).
Tokunaga, et al., Involvement of Linear Polyubiquitin of NEMO in NF-kB activation, Nature Cell Biol., 11(2):123-132 (2009) + Supplemental Information.
Behrends and Harper, "Constructing and decoding unconventional ubiquitin chains", Nature Structural and Molecular Biol., 18(5):520-28 (2011).
PCT International Search Report for PCT/EP2012/003987, dted Jan. 24, 2013, all pages.

* cited by examiner

*Primary Examiner* — Suzanne M Noakes
(74) *Attorney, Agent, or Firm* — Convergent Law Group LLP

(57) ABSTRACT

There is described a method for analyzing ubiquitin polymers using linkage-specific deubiquitinase enzymes. Novel specificities of deubiquitinase enzymes are also provided.

11 Claims, 13 Drawing Sheets

SEQUENCE LISTING

<160> NUMBER OF SEQ ID NOS: 4

<210> SEQ ID NO 1
<211> LENGTH: 4

```
<212> TYPE: PRT
<213> ORGANISM: Homo sapiens

<400> SEQUENCE: 1

Thr Arg Thr Val
1

<210> SEQ ID NO 2
<211> LENGTH: 4
<212> TYPE: PRT
<213> ORGANISM: Homo sapiens

<400> SEQUENCE: 2

Lys Leu Arg Glu
1

<210> SEQ ID NO 3
<211> LENGTH: 352
<212> TYPE: PRT
<213> ORGANISM: Homo sapiens

<400> SEQUENCE: 3

Met Ser Arg Gly Thr Met Pro Gln Pro Glu Ala Trp Pro Gly Ala Ser
1               5                   10                  15

Cys Ala Glu Thr Pro Ala Arg Glu Ala Ala Thr Ala Arg Asp Gly
            20                  25                  30

Gly Lys Ala Ala Ala Ser Gly Gln Pro Arg Pro Glu Met Gln Cys Pro
        35                  40                  45

Ala Glu His Glu Glu Asp Met Tyr Arg Ala Ala Asp Glu Ile Glu Lys
    50                  55                  60

Glu Lys Glu Leu Leu Ile His Glu Arg Gly Ala Ser Glu Pro Arg Leu
65                  70                  75                  80

Ser Val Ala Pro Glu Met Asp Ile Met Asp Tyr Cys Lys Lys Glu Trp
                85                  90                  95

Arg Gly Asn Thr Gln Lys Ala Thr Cys Met Lys Met Gly Tyr Glu Glu
            100                 105                 110

Val Ser Gln Lys Phe Thr Ser Ile Arg Arg Val Arg Gly Asp Asn Tyr
        115                 120                 125

Cys Ala Leu Arg Ala Thr Leu Phe Gln Ala Met Ser Gln Ala Val Gly
    130                 135                 140

Leu Pro Pro Trp Leu Gln Asp Pro Glu Leu Met Leu Leu Pro Glu Lys
145                 150                 155                 160

Leu Ile Ser Lys Tyr Asn Trp Ile Lys Gln Trp Lys Leu Gly Leu Lys
                165                 170                 175

Phe Asp Gly Lys Asn Glu Asp Leu Val Asp Lys Ile Lys Glu Ser Leu
            180                 185                 190

Thr Leu Leu Arg Lys Lys Trp Ala Gly Leu Ala Glu Met Arg Thr Ala
        195                 200                 205

Glu Ala Arg Gln Ile Ala Cys Asp Glu Leu Phe Thr Asn Glu Ala Glu
    210                 215                 220

Glu Tyr Ser Leu Tyr Glu Ala Val Lys Phe Leu Met Leu Asn Arg Ala
225                 230                 235                 240

Ile Glu Leu Tyr Asn Asp Lys Glu Lys Gly Lys Glu Val Pro Phe Phe
                245                 250                 255

Ser Val Leu Leu Phe Ala Arg Asp Thr Ser Asn Asp Pro Gly Gln Leu
            260                 265                 270
```

```
Leu Arg Asn His Leu Asn Gln Val Gly His Thr Gly Gly Leu Glu Gln
        275                 280                 285

Val Glu Met Phe Leu Leu Ala Tyr Ala Val Arg His Thr Ile Gln Val
290                 295                 300

Tyr Arg Leu Ser Lys Tyr Asn Thr Glu Phe Ile Thr Val Tyr Pro
305                 310                 315                 320

Thr Asp Pro Pro Lys Asp Trp Pro Val Val Thr Leu Ile Ala Glu Asp
                    325                 330                 335

Asp Arg His Tyr Asn Ile Pro Val Arg Val Cys Glu Glu Thr Ser Leu
                340                 345                 350

<210> SEQ ID NO 4
<211> LENGTH: 271
<212> TYPE: PRT
<213> ORGANISM: Homo sapiens

<400> SEQUENCE: 4

Met Ala Ala Glu Glu Pro Gln Gln Gln Lys Gln Glu Pro Leu Gly Ser
1               5                   10                  15

Asp Ser Glu Gly Val Asn Cys Leu Ala Tyr Asp Glu Ala Ile Met Ala
            20                  25                  30

Gln Gln Asp Arg Ile Gln Gln Glu Ile Ala Val Gln Asn Pro Leu Val
        35                  40                  45

Ser Glu Arg Leu Glu Leu Ser Val Leu Tyr Lys Glu Tyr Ala Glu Asp
    50                  55                  60

Asp Asn Ile Tyr Gln Gln Lys Ile Lys Asp Leu His Lys Lys Tyr Ser
65                  70                  75                  80

Tyr Ile Arg Lys Thr Arg Pro Asp Gly Asn Cys Phe Tyr Arg Ala Phe
                85                  90                  95

Gly Phe Ser His Leu Glu Ala Leu Leu Asp Asp Ser Lys Glu Leu Gln
            100                 105                 110

Arg Phe Lys Ala Val Ser Ala Lys Ser Lys Glu Asp Leu Val Ser Gln
        115                 120                 125

Gly Phe Thr Glu Phe Thr Ile Glu Asp Phe His Asn Thr Phe Met Asp
    130                 135                 140

Leu Ile Glu Gln Val Glu Lys Gln Thr Ser Val Ala Asp Leu Leu Ala
145                 150                 155                 160

Ser Phe Asn Asp Gln Ser Thr Ser Asp Tyr Leu Val Val Tyr Leu Arg
                165                 170                 175

Leu Leu Thr Ser Gly Tyr Leu Gln Arg Glu Ser Lys Phe Phe Glu His
            180                 185                 190

Phe Ile Glu Gly Gly Arg Thr Val Lys Glu Phe Cys Gln Gln Glu Val
        195                 200                 205

Glu Pro Met Cys Lys Glu Ser Asp His Ile His Ile Ala Leu Ala
210                 215                 220

Gln Ala Leu Ser Val Ser Ile Gln Val Glu Tyr Met Asp Arg Gly Glu
225                 230                 235                 240

Gly Gly Thr Thr Asn Pro His Ile Phe Pro Glu Gly Ser Glu Pro Lys
                245                 250                 255

Val Tyr Leu Leu Tyr Arg Pro Gly His Tyr Asp Ile Leu Tyr Lys
            260                 265                 270
```

UBIQUITIN CHAIN ANALYSIS

CROSS REFERENCE TO RELATED APPLICATIONS

This application is a national phase filing under 35 U.S.C. 371 of International Patent Application No. PCT/EP2012/003987, filed Sep. 24, 2012, which claims the benefit of GB Application No. 1211446.8, filed Jun. 26, 2012, and GB Application No. 1116526.3, filed Sep. 23, 2011, and is incorporated herein by reference.

The present invention relates to the analysis of polyubiquitin chains in order to determine the linkage type(s) present in the chain. In particular, the invention relates to the use of OTU DUB enzymes with a defined linkage specificity to selectively disassemble polyubiquitin chains, thus revealing the linkage type present in the polymer.

INTRODUCTION

Protein ubiquitination is a versatile posttranslational modification with roles in protein degradation, cell signaling, intracellular trafficking and the DNA damage response (Chen and Sun, 2009; Komander, 2009). Ubiquitin (Ub) polymers are linked through one of seven internal lysine (K) residues or through the N-terminal amino group. Importantly, the type of ubiquitin linkage determines the functional outcome of the modification chains. Possible linkages include K6, K11, K27, K29, K33, K48 and K63 linkages, or linkage to the N-terminus of a proximal unit (Komander, 2009). The best-studied ubiquitin polymers, K48- and K63-linked chains, have degradative and non-degradative roles, respectively (Chen and Sun, 2009; Hershko and Ciechanover, 1998). Recent data has revealed an unexpected high abundance of so-called atypical ubiquitin chains; for example, K11 linkages have been found to be as abundant as K48-linkages in S. cerevisiae (Peng et al., 2003; Xu et al., 2009). In our International patent application PCT/GB2011/000704 we describe the synthesis of K11 linked polyubiquitin.

Very little is known about the remaining linkage types. K6-linked Ub chains represent an enigmatic chain type that is readily detected in yeast (Xu et al, 2009) and mammalian cells (Dammer et al, 2011). This chain type has been linked to DNA repair processes since the BRCA1/BARD1 Ub ligase complex was reported to assemble K6-linkages (Morris & Solomon, 2004; Nishikawa et al, 2004; Wu-Baer et al, 2003). The related Ring1B/Bmi1 polycomb E3 ligase complex assembles heterotypic Ub chains with branches at K6, K27 and K48 (Ben-Saadon et al, 2006). However the cellular roles of K6-linkages are currently unclear, and further insight into K6-linkages has been hindered by the lack of tools. We recently reported chemical synthesis of K6-linked Ub dimers (K6 diUb), and preliminary structural insights into this chain type suggested novel compact chain conformations (Virdee et al, 2010). However, enzymatic systems to assemble, bind or disassemble K6-linkages in vitro have not been reported.

Ubiquitin chains are assembled by an enzymatic cascade comprising E1 Ub activating, E2 Ub conjugating, and E3 Ub ligating enzymes (Dye & Schulman, 2007). Two mechanistic classes of E3 ligases transfer Ub either directly to a substrate (RING and U-box E3s, (Deshaies & Joazeiro, 2009)) or first form a stable thioester intermediate with Ub (HECT (Rotin & Kumar, 2009) and members of RING-in-between-RING family (Wenzel et al, 2011)) before substrate modification. Once a Ub chain is formed, it is recognized by Ub receptors that contain Ub binding domains (UBDs) (Dikic et al, 2009) and mediate downstream effects such as shuttling the protein to the proteasome. Ubiquitination is reversible and deubiquitinases (DUBs) hydrolyse Ub chains (Komander et al, 2009a; Reyes-Turcu et al, 2009). Importantly, assembly, recognition and hydrolysis of Ub chains can be highly linkage specific, suggesting non-redundant and/or regulated functions of the individual chain types (Komander, 2009).

Accordingly, analysis of naturally occurring ubiquitiniation is important in order to assess the likely function of the ubiquitination process being studied.

However, the architecture of heterotypic Ub chains is difficult to assess by current technologies such as mass-spectroscopy (Dammer & Peng, 2010). Accordingly, it is difficult to determine if the K48 or K6 linkages are a significant component of the polyubiquitin chains produced, or a minor artifact.

The human genome encodes approximately 79 deubiquitinases (DUBs; also known as deubiquitylating or deubiquitinating enzymes) that are predicted to be active and which oppose the function of E3 ligases (Scheel, H. Comparative Analysis of the Ubiquitin-Proteasome System in *Homo sapiens* and *Saccharomyces cerevisiae*. Thesis, Univ. Cologne (2005); Nijman, S. M. et al. *Cell* 123, 773-786 (2005)). They can be subdivided into five families: ubiquitin C-terminal hydrolases (UCHs), ubiquitin-specific proteases (USPs), ovarian tumour proteases (OTUs), Josephins and JAB1/MPN/MOV34 metalloenzymes (JAMMs; also known as MPN+ and sometimes referred to as JAMM/MPN+). The UCH, USP, OTU and Josephin families are Cys proteases, whereas the JAMM/MPN+ family members are zinc metalloproteases.

There is a need in the art for a procedure to determine linkage specificity of polyubiquitin chains. In the prior art, such a procedure has been rendered difficult as tools which distinguished the various linkages were not available, or were insufficiently characterized as to their specificity.

SUMMARY OF THE INVENTION

We have determined that OTU family deubiquitinase (DUB) enzymes have linkage specificities which can be defined and exploited to provide tools for characterizing polyubiquitin chains. We have newly characterised the specificities of a number of OTU family DUBs, and provide methods for generating new linkage specificities, in order to provide a comprehensive system for polyubiquitin analysis.

In a first aspect, therefore, there is provided a method for determining the linkage specificity in a polyubiquitin chain, comprising the steps of:
(a) contacting an ubiquitin polymer with a first linkage-specific deubiquitinase enzyme under conditions in which the enzyme catalyses the disassociation of one or more, but less than seven, ubiquitin linkages;
(b) analysing the product of the catalysis for the presence of lower molecular weight fractions of the ubiquitin polymer; and
(c) repeating steps (a) and (b) in the presence of a second, different linkage-specific deubiquitinase.

In one embodiment, the deubiquitinase enzyme is an OTU family DUB.

A linkage-specific deubiquitinase has a defined specificity, and only disassociates certain linkages at reaction conditions. In one embodiment, the deubiquitinase catalyses the dissociation of two or fewer linkage types. In one embodiment, the deubiquitinase catalyses the dissociation of three or fewer linkage types. In one embodiment, the deubiquitinase catalyses the dissociation of four or fewer linkage types. In one embodiment, the deubiquitinase catalyses the dissociation of five or fewer linkage types. In one embodiment, the deubiquitinase catalyses the dissociation of six or fewer linkage types. In one embodiment, the deubiquitinase catalyses the disassociation of a single linkage type.

Analysis of the ubiquitin polymer requires the analysis of the product of the enzymatic disassociation (catalysis) reaction, to determine if monomers or polymers of ubiquitin have been released from the original ubiquitin polymer as a result of the action of the enzyme. In one embodiment, the product of the catalysis reaction is analysed by gel electrophoresis. Other techniques may be used, including size exclusion chromatography. In some embodiments, ubiquitin monomers and/or polymers may be labelled, for example using fluorescent dyes.

Fractions of the ubiquitin polymer being analysed may have a lower molecular weight, due to the removal of at least one monomer. The lower molecular weight fractions comprise ubiquitin monomers and/or polymers. The presence of a lower molecular weight fraction indicates successful disassociation by the deubiquitinase enzyme.

The steps can be repeated with one or more further deubiquitinase enzymes, in order to assay for the presence of linkages which are not disassociated by the first deubiquitinase. Different deubiquitinases can have overlapping or non-overlapping specificities; the design of the assay should make allowance for possible overlaps.

In a further aspect, there is provided a method according to the preceding aspect, wherein OTUD1 is used to cleave K63 linkages.

In one embodiment, OTUD4 is used to cleave K48 linkages.

In one embodiment, OTUD3 is used to cleave K6 and/or K11 linkages.

In a further aspect, there is provided the use of OTUD1 to cleave K63 linkages in an ubiquitin polymer.

One embodiment provides the use of OTUD4 to cleave K48 linkages in an ubiquitin polymer.

One embodiment provides the use of OTUD3 to cleave K6 and/or K11 linkages in an ubiquitin polymer.

One further embodiment provides the use of Fam105B/OTULIN to cleave M1 linkages in an ubiquitin polymer.

In a still further aspect, there is provided a kit for analysing an ubiquitin polymer, comprising two or more linkage-specific deubiquitinase enzymes.

We have identified, and provide herein, specificities for DUB enzymes which make available linkage-specific deubiquitinase enzymes which can, between them, disassemble every ubiquitin linkage. In one embodiment, the kit comprises sufficient DUBs to encompass every specificity and permit analysis of every potential ubiquitin polymer.

In one embodiment, the linkage-specific deubiquitinase enzymes are OTU DUBs.

In one embodiment, the linkage-specific deubiquitinase enzymes comprise one or more members of two or more of the following groups of enzymes: group 1 (Cezanne 1, Cezanne 2, yeast Otu1, YOD1 catalytic domain); group 2 (OTUD1, AMSH, OTUB2); group 3 (OTUB1, A20, OTUD4, OTULIN); group 4 (OTUD3); group 5 (TRABID); and group 6 (OTUD2/YOD1).

In one embodiment, the kit comprises at least one member of each of the 6 groups of enzymes recited above.

It should be noted that AMSH is not an OTU family enzyme; it is a JAMM family enzyme. Nevertheless, it displays linkage specificity.

In one embodiment, we have determined that the previously unannotated protein Fam105B id an OTU DUB, which we have named OTULIN. This DUB has a unique specificity for Met-1 linked polyubiquitin chains.

In a further embodiment, the kit may further comprise at least one of (a) a buffer comprising Tris pH 7.5, a chloride ion source and a reducing agent; and (b) instructions for use. The chloride ion source can be NaCl, and the reducing agent can be DTT.

The domain structure of OTU domain DUBs. For more detail, see Komander, 2009a.

Figure 5:
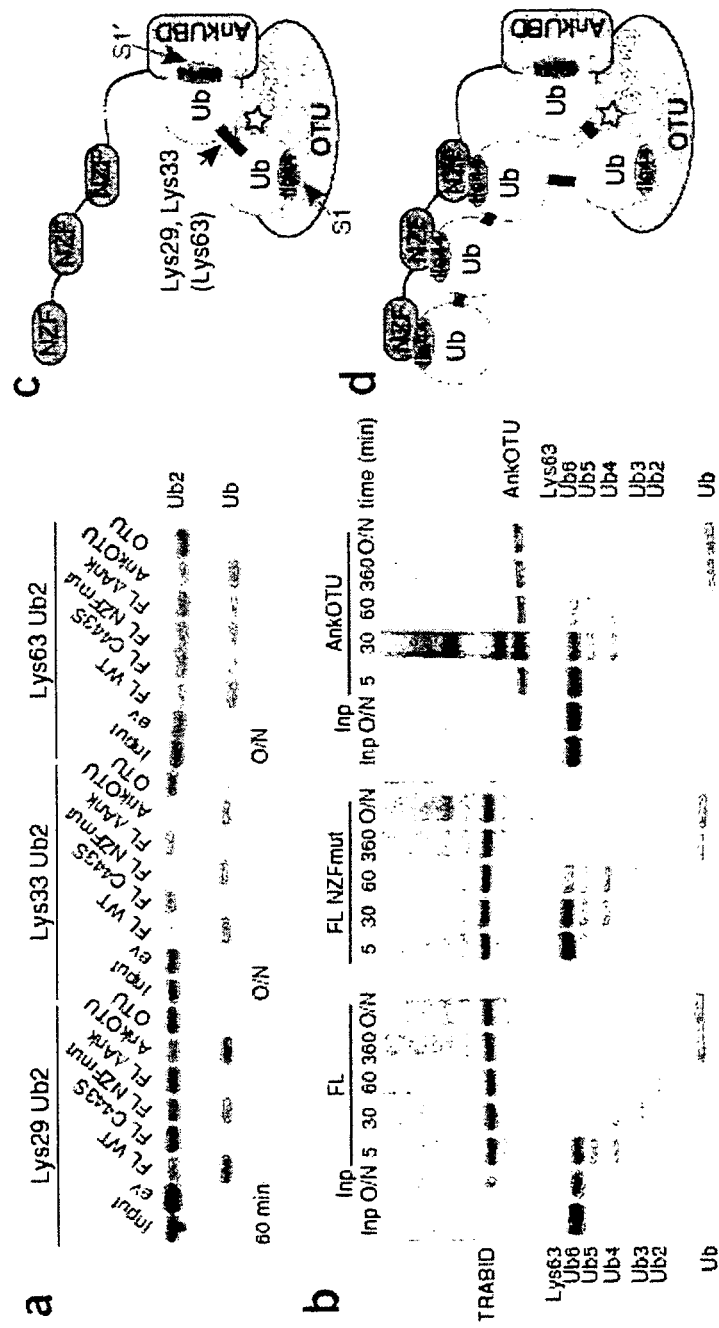
Figure 5:
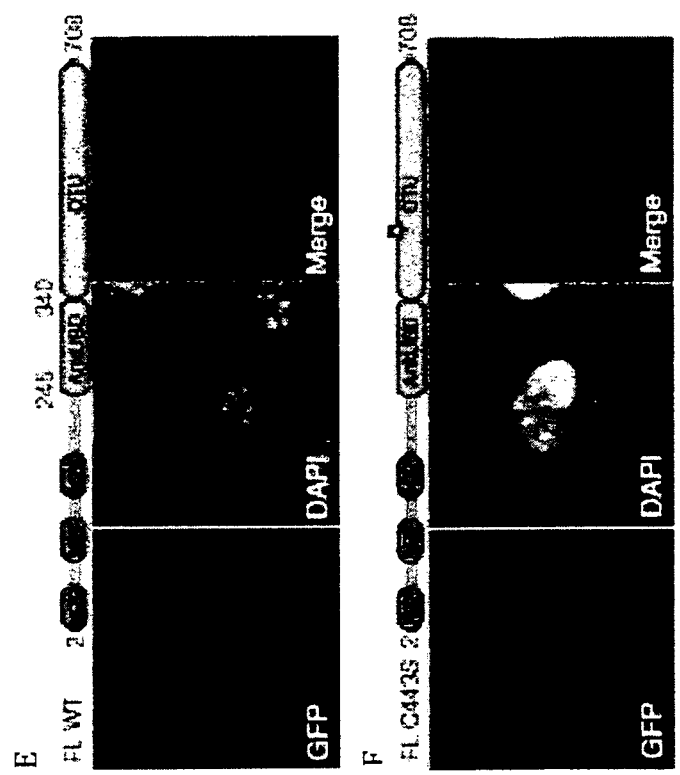

FIG. 5: TRABID UBD determines specificity

Role of the NZF domains in cleaving longer ubiquitin chains. Mammalian TRABID variants were incubated with polyubiquitin substrates for indicated times and visualized by silver staining. (a) Activity of TRABID variants against Lys29, Lys33 and Lys63-linked diubiquitin (Ub2) at indicated time point. Full-length C443S, catalytic mutant; full-length NZFmut, full-length with mutations in all three NZF domains; FL ΔAnk, full-length, lacking AnkUBD; AnkOTU, crystallized fragment; OTU, OTU domain. (b) Time-course analysis of mammalian full-length TRABID, full-length NZFmut and AnkOTU activity toward Lys63-linked hexaubiquitin. (c) Model for the role of the AnkUBD as an S1' ubiquitin-binding site in TRABID. (d) Model for the additional contribution of the NZF domains in cleaving longer polyubiquitin chains. (e) In vivo DUB assay NZF and AnkUBD are essential for TRABID puncta. Localization studies with GFP-TRABID in COS-7 cells 18 h after transfection (left). Nuclei are stained using DAPI (middle). The right image is a merge of the channels. The domain structure of TRABID is shown above. (f) A GFP-tagged full-length TRABID catalytic mutant (C443S; a yellow star in the domain representation indicates the mutation) adopts a punctate localization in COS-7 (shown) and other cell types FIG. 6: Alteration of specificity Analysis of TRABID DUB activity. (a) Bacterial TRABID variants were incubated with polyubiquitin substrates for indicated times and visualized by silver staining. Comparison of activity and specificity of the isolated OTU domain (above, [E] 1.2 µM) with TRABID AnkOTU (below, [E] 0.2 µM). Input enzyme levels are shown in OTU panel. Ub, ubiquitin. (b-e) Mammalian TRABID variants were incubated with polyubiquitin substrates for indicated times and visualized by silver staining. Flag-tagged TRABID variants were purified from HEK293 cells and used in DUB assays. (b) Specificity of mammalian full-length (FL), AnkOTU and OTU TRABID against the diubiquitin panel after overnight (O/N, 16 h) incubation. (c) Time-course analysis of mammalian TRABID variants against its substrate linkages. FL ΔAnk means full-length, lacking AnkUBD. Input (Inp) controls highlight the stability of ubiquitin substrates in the absence of enzyme in the reaction mixture. (d) Activity of full-length TRABID with point mutations in the AnkUBD against its preferred diubiquitin substrates. Full-length C443S, catalytic mutant. DUB activity assays carried out with material obtained from Flag-empty vector (ev) immunoprecipitation showed no activity. (e) Time-course activity of TRABID variants against Lys63-linked hexaubiquitin.

Figure 7:
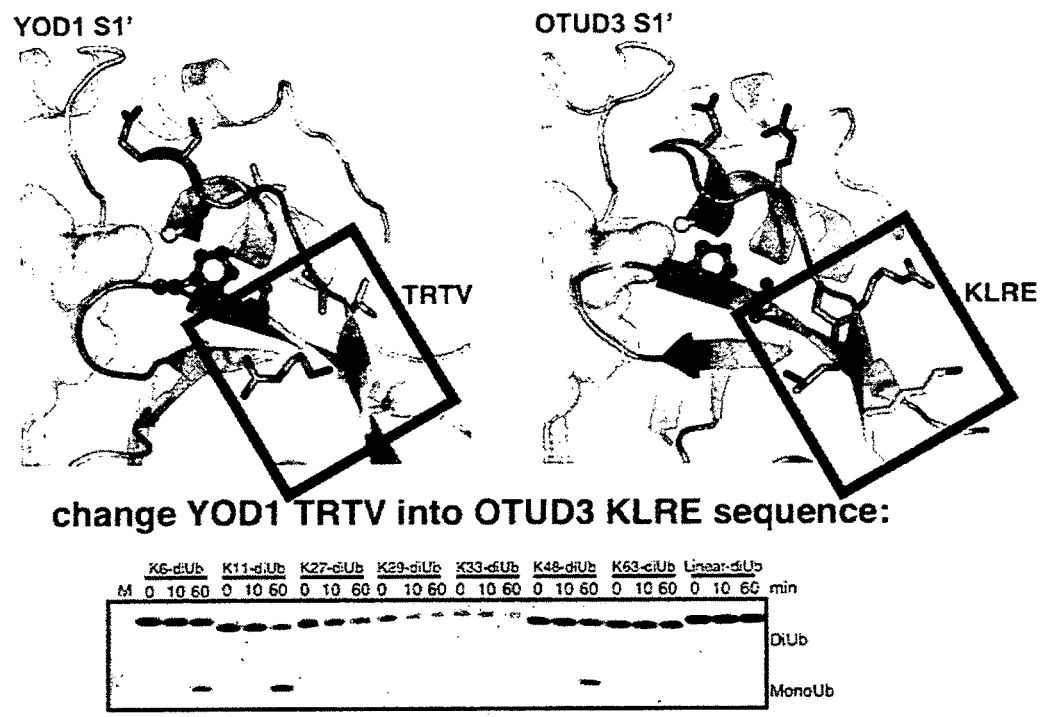

FIG. 7: Alteration of specificity

Mutation of TRTV sequence in YOD1 to KLRE, matching homologous sequence in OTUD3, results in alteration of cleavage specificity (lower panel).

Figure 8:
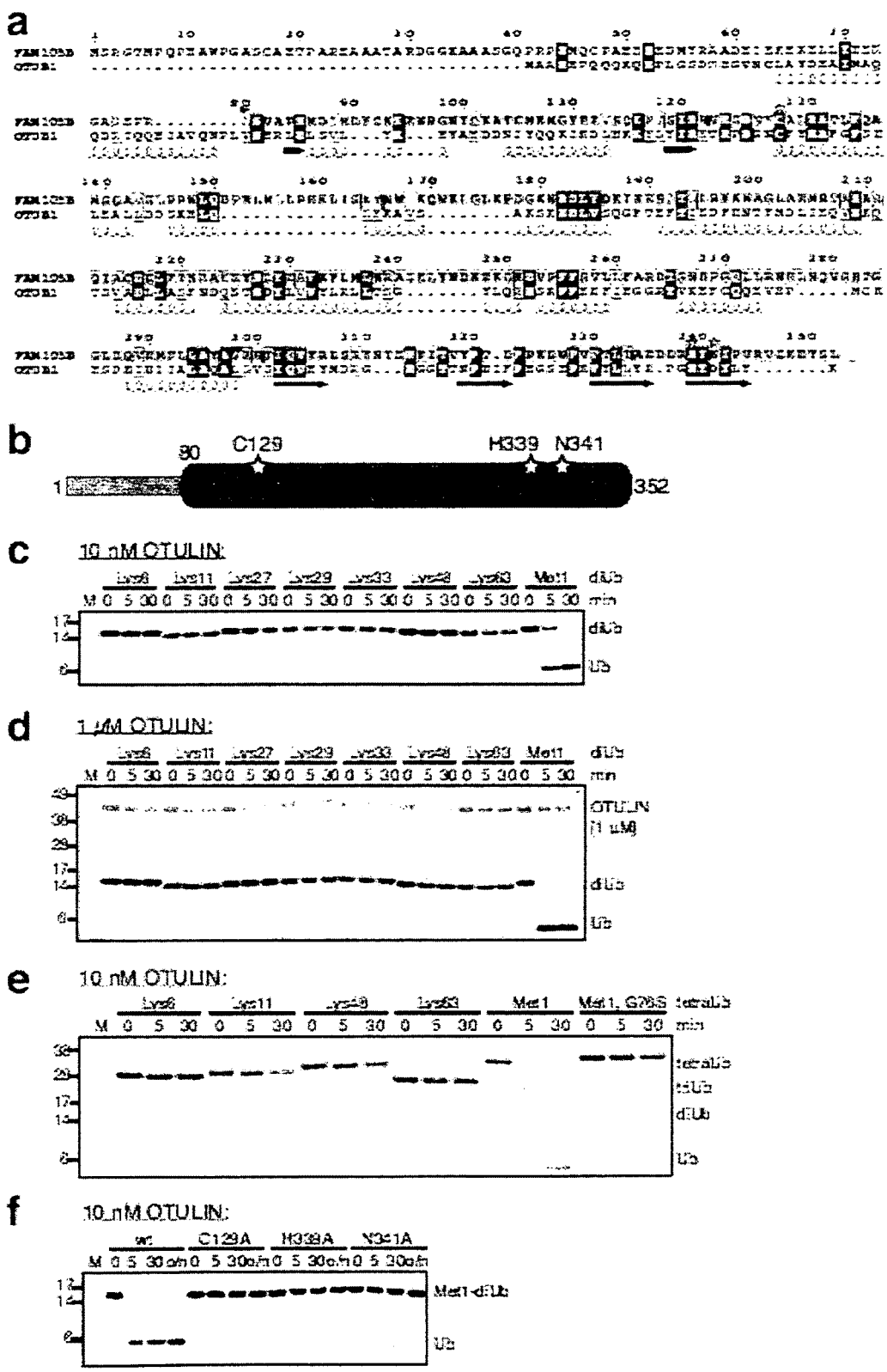

FIG. 8: OTULIN substrate specificity a) Sequence alignment of FAM105B/OTULIN (SEQ ID No. 3) with OTUB1 (SEQ ID No. 4). Secondary structure elements are shown for OTUB1. The OTU domain is indicated in blue, and catalytic residues are labeled with yellow stars. b) Domain structure of OTULIN, colored as in a. c, d) Linkage specificity of OTULIN. DiUb (1 µM) of all possible linkage types is hydrolyzed over a time course by 10 nM (c) or 1 µM (d) OTULIN, and visualized on silver stained 4-12% gradient SDS PAGE gels. OTULIN protein is visible in d. e) Cleavage of tetraUb chains, as in c. The last substrate is a Met1-tetraUb with G76S mutation in the Ub linkage. f) Hydrolysis of Met1-diUb by wild-type and mutant OTULIN.

DETAILED DESCRIPTION OF THE INVENTION

Unless defined otherwise, all technical and scientific terms used herein have the same meaning as commonly understood by those of ordinary skill in the art, such as in the arts of peptide chemistry, cell culture, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.). All publications cited herein are incorporated herein by reference in their entirety for the purpose of describing and disclosing the methodologies, reagents, and tools reported in the publications that might be used in connection with the invention.

A polyubiquitin chain or polymer is a chain of at least two ubiquitin monomers covalently linked together. Ubiquitin chains are formed using 7 possible linkages at defined Lys residues, including K6, K11, K27, K29, K33, K48 and K63 linkages, or linkage to the N-terminus of a proximal unit. A single linkage refers to linkage at one of K6, K11, K27, K29, K48 and K63, or the M1 linkage.

Ubiquitin polymers can be derived from any source, including ubiquitin monomers polymerised in vitro (see, for example, out international patent application PCT/GB2011/000704). Ubiquitin polymers can be obtained from cells or in vivo as a result of observed ubiquitination by natural processes. The nature of the linkages present in the polymer can influence the role of the ubiquitination which is being observed. In one embodiment, therefore, the ubiquitin polymer is a polyubiquitin chain obtained as a result of ubiquitination by natural processes.

Deubiquitinase enzymes (DUBs) are enzymes which disassociate ubiquitin polymers. For a review, see Komander, 2009a. We describe herein linkage-specific DUBs which are useful in disassembling particular ubiquitin linkages. For example, OTU domain DUBs are provided with specificities for any desired linkage. OTU domains fall into three structural sub-categories, the OTU domains, five A20-like OTU domains and two Otubains (see Komander, 2009a).

DUBs have different specificities if they disassociate monomers bound together by different linkages. The specificities can be non overlapping, for example as in the case of Cezanne 1 (which is K11 specific) and OTUB1, which is K48 specific. Alternatively, they can be overlapping, as in the case of OTUD3, which cleaves K11 and K6, and OTUD2, which cleaves K11, K27 and K33.

A lower molecular weight fraction of an ubiquitin polymer is a monomer or polymer from which at least one ubiquitin monomer has been removed as a result of disassembly by a DUB.

The presence or absence of monomers and polymers can be performed by any technique which measures changes in size, or the dissociation of monomers from polymers.

A kit, as referred to herein, is a combination package comprising two or more entities which can be used together, or in sequence, for analysing ubiquitin monomers. Kits can comprise reagents packaged in appropriate containers, buffers and test materials, including for example ubiquitin monomers and polymers intended for validation of assays. Kits can moreover include instructions as to their proper use.

Enzymes

Deubiquitinase enzymes for use in conjunction with the present invention are known in the art and can be produced by conventional means. See, for example, Komander 2009a and references cited therein, which are incorporated herein by reference. Linkage-specific DUBs have been characterised herein for the first time; the following table describes the linkage specificity of DUB enzymes useful in the present invention. The linkages cleaved by various enzymes are set forth in Table 1.

TABLE 1

The DUBs are identified as full length (FL) or individual domains.
3 = preferred chain linkage cleavage; 2 = some cleavage;
1 = negligible cleavage; 0 = no cleavage.

| DUB | K6 | K11 | K27 | K29 | K33 | K48 | K63 | M1 |
|---|---|---|---|---|---|---|---|---|
| OTUD1 FL | 0 | 0 | 0 | 0 | 0 | 0 | 3 | 0 |
| OTUD1 OTU + UIM | 0 | 0 | 0 | 0 | 0 | 0 | 3 | 0 |
| OTUD1 OTU | 0 | 2 | 3 | 3 | 3 | 3 | 2 | 0 |
| OTUD1 tOTU + UIM | 3 | 3 | 1 | 1 | 1 | 3 | 3 | 0 |
| OTUD2 FL | 1 | 2 | 3 | 3 | 3 | 2 | 0 | 0 |
| OTUD2 OTU + ZnF | 1 | 2 | 3 | 3 | 3 | 2 | 0 | 0 |
| OTUD2 OTU | 0 | 3 | 1 | 1 | 1 | 2 | 0 | 0 |
| OTUD3 OTU + UBA | 3 | 3 | 1 | 1 | 1 | 1 | 1 | 0 |
| OTUD3 OTU | 3 | 3 | 1 | 1 | 1 | 1 | 1 | 0 |
| OTUD4 OTU | 1 | 1 | 1 | 0 | 0 | 3 | 1 | 0 |
| OTUD5 OTU | 0 | 0 | 0 | 0 | 0 | 0 | 0 | 0 |
| OTUD5 pOTU | 2 | 2 | 1 | 1 | 1 | 3 | 3 | 0 |
| OTUD6A FL | 0 | 2 | 3 | 3 | 3 | 2 | 1 | 0 |
| OTUD6B FL | 0 | 0 | 0 | 0 | 0 | 0 | 0 | 0 |
| OTUB1 FL | 0 | 0 | 0 | 0 | 0 | 3 | 0 | 0 |
| OTUB2 FL | 0 | 2 | 0 | 0 | 0 | 2 | 3 | 0 |
| A20 OTU | 0 | 2 | 0 | 0 | 0 | 3 | 0 | 0 |
| Cezanne OTU | 0 | 3 | 0 | 0 | 0 | 0 | 0 | 0 |
| Cezanne 2 OTU | 0 | 3 | 0 | 0 | 0 | 0 | 0 | 0 |
| TRABID OTU + AnkUBD | 0 | 0 | 0 | 3 | 3 | 0 | 2 | 0 |
| VCPIP OTU | 0 | 3 | 0 | 0 | 0 | 3 | 0 | 0 |
| OTULIN | 0 | 0 | 0 | 0 | 0 | 0 | 0 | 3 |

Other DUBs are known which have a lower level of specificity. These include USP21 (Ye et al EMBO Rep, 2011); viral OTU domains (Akutsu et al, PNAS 2011).

The following information is currently available about OTU family DUBs in the NCBI protein database.

1. OTUB1

Official Symbol: OTUB1 and Name: OTU domain, ubiquitin aldehyde binding 1[*Homo sapiens*]

Other Aliases: HSPC263, FLJ20113, FLJ40710, MGC111158, MGC4584, OTB1, OTU1

Other Designations: OTTHUMP00000236859; OTTHUMP00000236860; OTTHUMP00000236862; OTTHUMP00000236863; OTTHUMP00000237236; OTU domain-containing ubiquitin aldehyde-binding protein 1; OTU-domain UbaI-binding 1; deubiquitinating enzyme OTUB1; hOTU1; otubain-1; ubiquitin thioesterase OTUB1; ubiquitin-specific protease otubain 1; ubiquitin-specific-processing protease OTUB1

Chromosome: 11; Location: 11q13.1

Annotation: Chromosome 11NC_000011.9 (63753325 . . . 63765892)

MIM: 608337

ID: 55611

2. OTUB2

Official Symbol: OTUB2 and Name: OTU domain, ubiquitin aldehyde binding 2[*Homo sapiens*]

Other Aliases: C14orf137, FLJ21916, MGC3102, OTB2, OTU2

Other Designations: OTU domain-containing ubiquitin aldehyde-binding protein 2; deubiquitinating enzyme OTUB2; otubain-2; ubiquitin thioesterase OTUB2; ubiquitin-specific protease otubain 2; ubiquitin-specific-processing protease OTUB2

Chromosome: 14; Location: 14q32.12

Annotation: Chromosome 14NC_000014.8 (94492724 . . . 94515276)

MIM: 608338

ID: 78990

3. OTUD1

Official Symbol: OTUD1 and Name: OTU domain containing 1[*Homo sapiens*]

Other Aliases: DUBA7, OTDC1

Other Designations: DUBA-7; OTTHUMP00000019312; OTU domain-containing protein

Chromosome: 10; Location: 10p12.2

Annotation: Chromosome 10NC_000010.10 (23728198 . . . 23731310)

MIM: 612022

ID: 220213

4. OTUD3

Official Symbol: OTUD3 and Name: OTU domain containing 3[*Homo sapiens*]

Other Aliases: RP11-91K11.3, DUBA4, KIAA0459, RP11-460G22.1

Other Designations: OTTHUMP00000002782; OTU domain-containing protein 3

Chromosome: 1; Location: 1p36.13

Annotation: Chromosome 1NC_000001.10 (20208888 . . . 20239438)

MIM: 611758

ID: 23252

5. OTUD4

Official Symbol: OTUD4 and Name: OTU domain containing 4[*Homo sapiens*]

Other Aliases: DKFZp434I0721, DUBA6, HIN1, HSHIN1, KIAA1046

Other Designations: HIV-1 induced protein HIN-1; HIV-1-induced protein HIN-1; OTTHUMP00000220308; OTTHUMP00000220309; OTTHUMP00000220310; OTTHUMP00000220423; OTTHUMP00000222760; OTU domain-containing protein 4

Chromosome: 4; Location: 4q31.21

Annotation: Chromosome 4NC_000004.11 (146054802 . . . 146100832, complement)

MIM: 611744

ID: 54726

6. OTUD5

Official Symbol: OTUD5 and Name: OTU domain containing 5[*Homo sapiens*]

Other Aliases: DKFZp761A052, DUBA, MGC104871

Other Designations: OTTHUMP00000025820; OTTHUMP00000025821; OTTHUMP00000025822; OTTHUMP00000226750; OTU domain-containing protein 5; deubiquinating enzyme A; deubiquitinating enzyme A Chromosome: X; Location: Xp11.23

Annotation: Chromosome XNC_000023.10 (48779301 . . . 48815648, complement)

MIM: 300713

ID: 55593

7. OTUD6A

Official Symbol: OTUD6A and Name: OTU domain containing 6A[*Homo sapiens*]

Other Aliases: DUBA2, FLJ25831, HSHIN6

Other Designations: DUBA-2; HIN-6 protease; OTTHUMP00000217295; OTU domain-containing protein 6A Chromosome: X; Location: Xq13.1

Annotation: Chromosome XNC_000023.10 (69282341 . . . 69284029)

MIM: 300714

ID: 139562

8. OTUD6B

Official Symbol: OTUD6B and Name: OTU domain containing 6B[*Homo sapiens*]

Other Aliases: CGI-77, DUBA5

Other Designations: DUBA-5; OTTHUMP00000198453; OTU domain-containing protein 6B Chromosome: 8; Location: 8q21.3

Annotation: Chromosome 8NC_000008.10 (92082424 . . . 92099323)

MIM: 612021

ID: 51633

9. OTUD7A

Official Symbol: OTUD7A and Name: OTU domain containing 7A[*Homo sapiens*]

Other Aliases: C15orf16, C16ORF15, CEZANNE2, OTUD7

Other Designations: OTTHUMP00000159599; OTU domain-containing protein 7A; cezanne 2; zinc finger protein Cezanne 2

Chromosome: 15; Location: 15q13.3

Annotation: Chromosome 15NC_000015.9 (31775329 . . . 31947542, complement)

MIM: 612024

ID: 161725

10. OTUD7B

Official Symbol: OTUD7B and Name: OTU domain containing 7B[*Homo sapiens*]

Other Aliases: RP11-212K13.2, CEZANNE, ZA20D1

Other Designations: OTTHUMP00000014192; OTTHUMP00000014193; OTU domain-containing protein 7B; cellular zinc finger anti-NF-kappa-B protein; cellular zinc finger anti-NF-kappaB Cezanne; zinc finger A20 domain-containing protein 1; zinc finger protein Cezanne; zinc finger, A20 domain containing 1

Chromosome: 1; Location: 1q21.2

Annotation: Chromosome 1NC_000001.10 (149912231 . . . 149982686, complement)

MIM: 611748

ID: 56957

11. TNFAIP3

Official Symbol: TNFAIP3 and Name: tumor necrosis factor, alpha-induced protein 3[*Homo sapiens*]

Other Aliases: RP11-35612.3, A20, MGC104522, MGC138687, MGC138688, OTUD7C, TNFA1P2

Other Designations: OTTHUMP00000017289; OTU domain-containing protein 7C; TNF alpha-induced protein 3; putative DNA-binding protein A20; tumor necrosis factor alpha-induced protein 3; tumor necrosis factor inducible protein A20; zinc finger protein A20 Chromosome: 6; Location: 6q23

Annotation: Chromosome 6NC_000006.11 (138188581 . . . 138204449)

MIM: 191163

ID: 7128

12. YOD1

Official Symbol: YOD1 and Name: YOD1 OTU deubiquinating enzyme 1 homolog (*S. cerevisiae*)[*Homo sapiens*]

Other Aliases: RP11-164023.1, DKFZp451J1719, DUBA8, OTUD2, PR00907

Other Designations: DUBA-8; HIN-7; HIV-1-induced protease 7; OTTHUMP00000034284; OTU domain containing 2; OTU domain-containing protein 2; YOD1 OTU deubiquinating enzyme 1 homolog (yeast); hsHIN7; ubiquitin thioesterase OTU1

Chromosome: 1; Location: 1q32.2

Annotation: Chromosome 1NC_000001.10 (207217194 . . . 207224422, complement)

MIM: 612023

ID: 55432

13. OTULIN (Fam105B)

Official Symbol: FAM105B and Name: family with sequence similarity 105, member B [*Homo sapiens*]

Other Designations: protein FAM105B

Chromosome: 5

Location:

5p15.2

Annotation: Chromosome 5, NC_000005.9 (14664783 . . . 14699842)

ID: 90268

Figure 4:
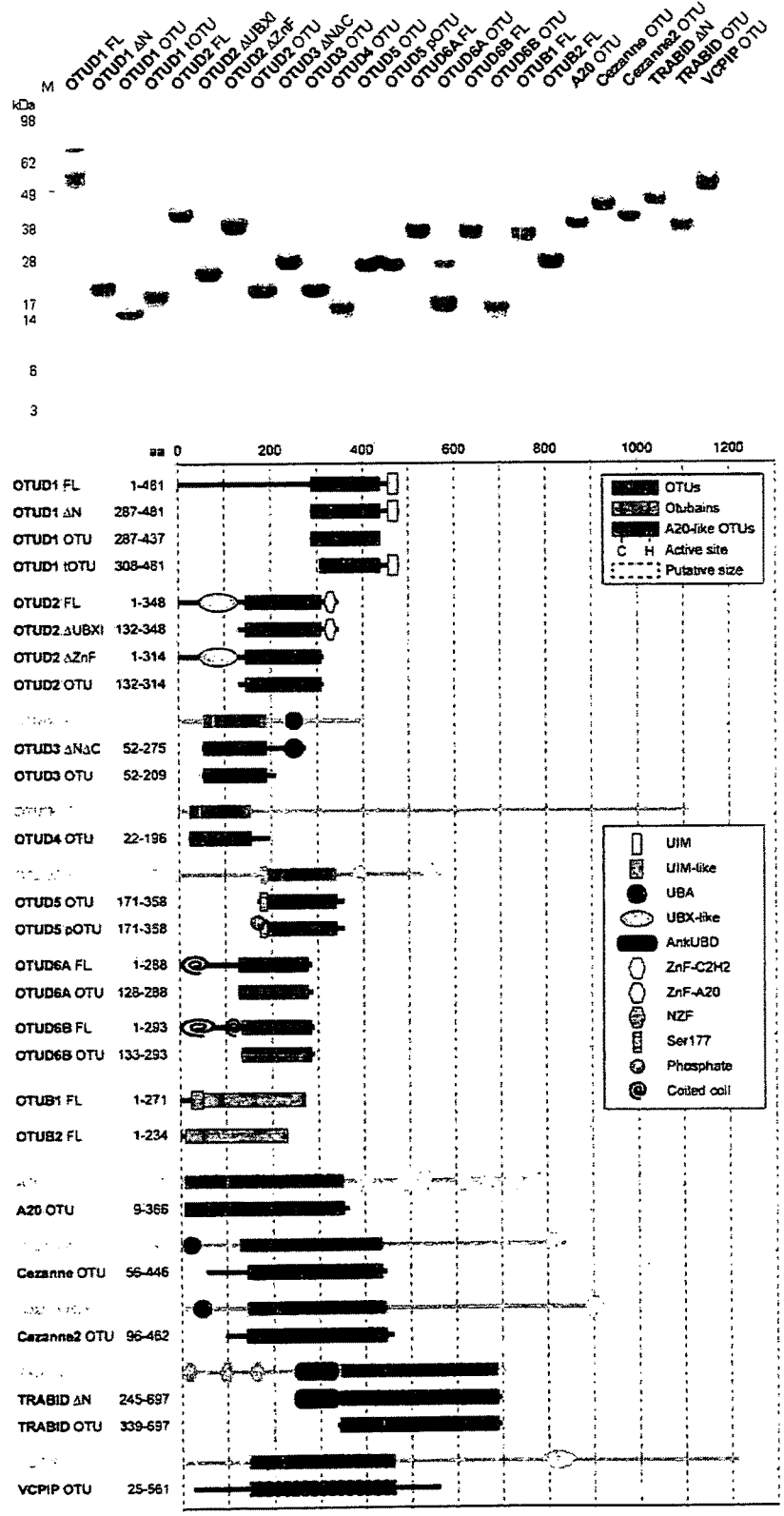
FIG. 4: OTU Domain DUBs (C) Analysis of vOTU, OTUB1 and OTUB3 Ub chain architecture of N1eL assembled Ub chains in vitro.

FIG. 4 shows the domains present in 33 different versions of 14 OTU domain DUBs.

Recombinant Expression of Enzymes

Expression of nucleic acids encoding DUBs can be carried out in any suitable expression system. Expressions systems are known in the art and may be obtained commercially or according to instructions provided in laboratory manuals.

A wide variety of expression systems are available for the production of chimeric polypeptides. For example, expression systems of both prokaryotic and eukaryotic origin may be used for the production of enzymes.

Nucleic acid vectors are commonly used for protein expression. The term "vector" refers to a nucleic acid molecule that may be used to transport a second nucleic acid molecule into a cell, and/or express it therein. In one embodiment, the vector allows for replication of DNA sequences inserted into the vector. The vector may comprise a promoter to enhance expression of the nucleic acid molecule in at least some host cells. Vectors may replicate autonomously (extrachromosomal) or may be integrated into a host cell chromosome. In one embodiment, the vector comprises an expression vector capable of producing a fusion protein derived from at least part of a nucleic acid sequence inserted into the vector.

A cloning vector can be a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An expression vector typically comprises a transcription promoter, a gene, and a transcription terminator. Expression vectors may be autonomously replicating, or integrated into the host genome. Gene expression is usually placed under the control of a promoter, and such a gene is said to be operably linked to the promoter. Similarly, a regulatory element and a core promoter are operably linked if the regulatory element modulates the activity of the core promoter. The nucleic acid encoding the chimeric enzyme according to the invention is typically expressed under the control of a promoter in an expression vector.

To express a gene, a nucleic acid molecule encoding the protein must be operably linked to regulatory sequences that control transcriptional expression and then, introduced into a host cell. In addition to transcriptional regulatory sequences, such as promoters and enhancers, expression vectors can include transcriptional and translational regulatory sequences. The sequences used will be appropriate to the host, which may be prokaryotic or eukaryotic. The transcriptional and translational regulatory signals suitable for a mammalian host may be derived from viral sources, such as adenovirus, bovine papilloma virus, simian virus, or the like, in which the regulatory signals are associated with a particular gene that has a high level of expression. Suitable transcriptional and translational regulatory sequences also can be obtained from mammalian genes, such as actin, collagen, myosin, and metallothionein genes. Prokaryotic regulatory sequences may similarly be derived from viral genes, and are known in the art.

The inclusion of an affinity tag is useful for the identification or selection of cells expressing the fusion protein. Examples of affinity tags include polyHistidine tags (which have an affinity for nickel-chelating resin), c-myc tags, which are detected with anti-myc antibodies, calmodulin binding protein (isolated with calmodulin affinity chromatography), substance P, the RYIRS tag (which binds with anti-RYIRS antibodies), a hemagglutinin A epitope tag, which is detected with an antibody, the Glu-Glu tag, and the FLAG tag (which binds with anti-FLAG antibodies). Nucleic acid molecules encoding such peptide tags are available, for example, from Sigma-Aldrich Corporation (St. Louis, Mo., USA).

The gram-negative bacterium E. coli is widely used as a host for heterologous gene expression. Although large amounts of heterologous protein can accumulate inside the cell, this expression system is effective in the context of the present invention. Suitable strains of E. coli include BL21 (DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647.

Bacteria from the genus Bacillus are also suitable as heterologous hosts, and have capability to secrete proteins into the culture medium. Other bacteria suitable as hosts are those from the genera Streptomyces and Pseudomonas.

Suitable strains of Bacillus subtilus include BR151, YB886, MI119, MI120, and B170 (see, for example, Hardy, "Bacillus Cloning Methods," in DNA Cloning: A Practical Approach, Glover (ed.) (IRL Press 1985)). Standard techniques for propagating vectors in prokaryotic hosts are well-known to those of skill in the art (see, for example, Ausubel 1995; Wu et al., Methods in Gene Biotechnology (CRC Press, Inc. 1997)).

Eukaryotic hosts such as yeasts or other fungi may be used. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable eukaryotic host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products.

In some embodiments, the fusion proteins may be expressed as GST fusions. For example, the pGEX and pOPIN vector systems may employ a GST fusion. Use of GST as a fusion partner provides an inducible expressions system which facilitates the production of proteins in the E. coli system. Proteins expressed using this system can be isolated using a glutathione capture resin.

For example, recombinant GST-OTUD1 constructs are expressed in Rosetta 2 (DE3) pLacI cells (Novagen). 1 L cultures of cells are induced at $OD_{600}$ of 0.6 with 250 µM IPTG and proteins are expressed at 20° C. overnight. Cells are harvested and flash-frozen. 30 ml lysis buffer containing 270 mM sucrose, 50 mM Tris (pH 8.0), 50 mM NaF, 1 protease inhibitor cocktail tablet (Roche) (0.1% v/v β-mercaptoethanol, 1 mg/ml lysozyme and 0.1 mg/ml DNase) are added per liter of culture. After sonication, cell lysates are cleared using a Sorvall SS-34 rotor (18,000 rpm, 30 min, 4° C.) and supernatants are incubated with Glutathione Sepharose 4B (GE Healthcare) for 1 h to immobilize soluble GST fusion proteins. Subsequently, the sepharose beads are washed with 500 ml high salt buffer [500 mM NaCl, 25 mM Tris (pH 8.5), 5 mM DTT] and 300 ml low salt buffer [150 mM NaCl, 25 mM Tris (pH 8.5), 5 mM DTT]. For site-specific cleavage of the GST tag, immobilized fusion proteins are incubated with 30 mM PreScission protease (GE Healthcare) overnight. Cleaved proteins are eluted with low salt buffer and flash-frozen in liquid nitrogen. All samples are >95% pure after purification.

Conservative Enzyme Mutation

The invention contemplates the use of natural enzymes that have been mutated. In some cases, the mutation is designed totter the activity or specificity of the enzyme 9 see below). In other cases, the mutation may be conservative, such that enzyme function is conserved. Conservative amino acid substitutions generally follow the following scheme:

| Side chain | Members |
| --- | --- |
| Hydrophobic | met, ala, val, leu, ile |
| Neutral hydrophilic | cys, ser, thr |
| Acidic | asp, glu |
| Basic | asn, gln, his, lys, arg |
| Residues that influence chain orientation | gly, pro |
| Aromatic | trp, tyr, phe |

In the above table, amino acids identified in the same row are considered to have similar side-chains and are can be substituted for each other with the least impact on protein structure and function.

Mutation can be at the nucleic acid level, that is changes may be effected to the nucleic acid encoding a relevant domain without changing the structure of the enzyme itself, as a result of redundancy in the genetic code. Such changes can, for example, confer improved expression in heterologous host cells by employing preferred codon usage patterns.

Other mutations will change the amino acid sequence of the enzyme. As noted above, this can take the form of additions to or deletions from the N and C termini of the protein. Moreover, changes may be made within the sequence of the enzyme, for example through substitution, addition or deletion of one or more amino acids. Conservative amino acid substitutions are preferred, as set forth above. For example, 1, 2, 3, 4, 5, 6, 7, 8, 9, 10, 15, 20 or more amino acids are added, deleted and/or substituted by other amino acids.

In a preferred embodiment, the naturally occurring enzyme is used.

Alteration of DUB Specificity

Although OTU family DUBs share the conserved OTU domain, their mechanism of action is not identical across the family. In particular, the provision of an S1' ubiquitin binding site, which determines recognition of the ubiquitin peptide, can occur in a number of ways.

There are four potential methods for S1' site provision in a DUB. These are (i) provision by a ubiquitin binding domain (UBD) in cis; (ii) S1' presence on the OTU domain itself; (iii) direct recognition of the linkage sequence; and (iv) provision of the S1' site by a UBD in trans.

Additional UBDs are present on at least eight known OTU DUBs, including OTUD1, OTUD3, OTUD5, YOD1/OTU1, A20, Cezanne, Cezanne 2 and TRABID (See FIG. 4). In Trabid, we have shown that the Ankyrin repeat (Ank) domain acts as a UBD and determines the linkage specificity, by interacting with the ubiquitin dimer (FIG. 5).

Figure 6:
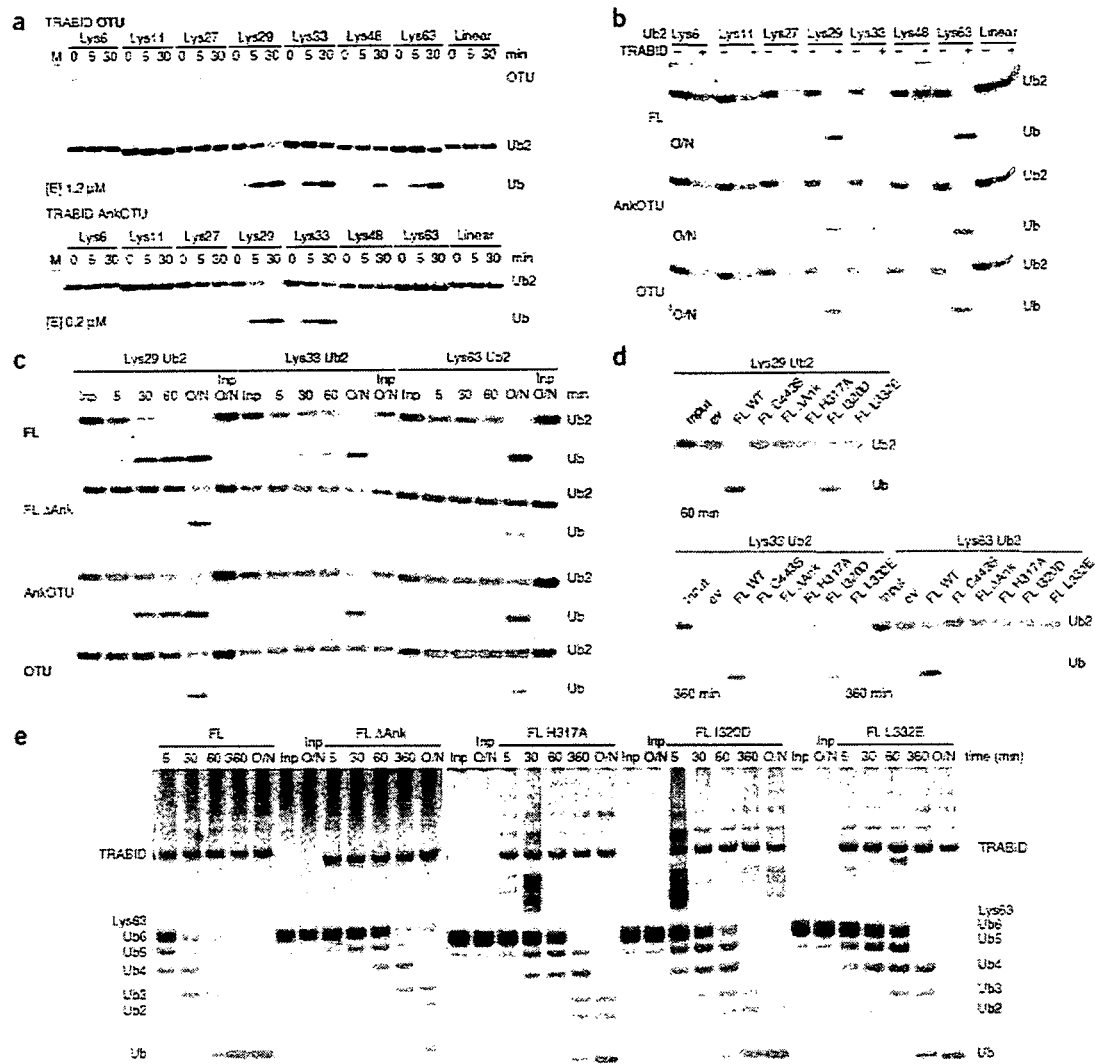

Removing the Ank repeat of Trabid results in a broadening of Trabid's specificity to include cleaving at K63 linkages, in addition to K29 and K33 linkages (FIG. 6). In YOD1/OTU1, removal of the ZnF UBD results in restriction of the specificity from K11, K27, K29 and K33 linkages to K11 linkages alone. Accordingly, the specificity of an OTU domain DUB can be altered by adding or removing UBD domains.

A second mechanism determining OTU specificity relies on the provision of an S1' ubiquitin site on the OTU domain itself. This renders certain OTU sites specific in isolation; for example, the YOD1 OTU domain is specific for K11 linkages.

Modification of the S1' site in a DUB can result in alteration of the specificity. For example, alteration of the YOD1 S1' site (TTRV) to match the sequence present in OTUD3 (KLRE) results in extension of the specificity of YOD1 to cleave K6 and K48 linkages, in addition to K11 linkages (FIG. 7). Mutation of the S1' ubiquitin binding site on the OTU domain can hence be used to modulate linkage specificity, and to engineer new specificities in known OTU domains.

Analysis of Polyubiquitin Chains

Analysis of polyubiquitin chains can be carried out by a number of means, including gel electrophoresis, size exclusion chromatography and other methods for separating compounds on the basis of size. Cleavage of polymers can e.g. be detected by silver staining using the Silver Stain Plus kit (BioRad), by coomassie staining, or by fluorescent staining methods.

In general, deubiquitination assays are performed using an appropriate concentration of DUB in a buffer comprising Tris pH7.5, a source of chloride ions and a reducing agent. For example, the buffer can comprise NaCl and DTT.

The concentration of DUBs should be adjusted to promote linkage-specific chain cleavage. For example, DUB enzymes can be incubated in the reaction mixture at a concentration of between 1 µM and 10 µM. In one embodiment, OTUD3 can be incubated at about 5.5 µM; OTUB1 at approximately 2.7 µM.

Applications of the methods of the invention are diverse. For example, the deubiquitinases described herein can be used to analyse the nature of polyubiquitin chains present on proteins which have been ubiquitinated in vivo or in vitro. This provides important information as to the function and role of the protein and the ubiquitination process.

In such an assay, monomers and polymers released from the polyubiquitin chain can be analysed to determine the presence or absence of linkages which are cleaved by the DUB in use. Since the linkages and sequence of linkages in polyubiquitin determines the post-translational processing of a protein, this method provides for sequencing polyubiquitin chains, which can provide information concerning the fate or intended fate of a protein in a cell.

In another example, ubiquitinated proteins in a cell can be isolated on a ubiquitin affinity resin, and analysed for the presence of particular ubiquitin linkages by exposing them to DUB enzymes and monitoring release of the protein from the matrix.

Inactivated linkage specific DUBs can be used to capture proteins bearing polyubiquitin chains having particular linkages. Inactive DUBs can be created by inactivating the DUB domain, by appropriate mutagenesis; for example, mutation of the active site cysteine to alanine results in an inactive DUB, while mutation to serine significantly reduces (but not abolishes) DUB activity. In Trabid, for example, the mutation C443S inactivates the DUB to more than 98%. This approach has significant advantages over that of, for example, Hjerpe et al., EMBO reports 2 Oct. 2009; doi: 10.1038/embor.2009.192, which discloses ubiquitin-binding agents which favour polymers over ubiquitin monomers, but are not linkage-specific.

The use of multiple inactivated DUBs can allow the isolation of proteins with specific linkages. DUBs linked to a solid phase can provide a resin to pull down specifically modified peptides.

Inactive DUBs can also be used to label ubiquitinated proteins at particular linkages. Labels, for example fluorescent labels, can be attached to deactivated DUBs and used to label polyubiquitin chains in a linkage-specific manner. This can be done intracellularly, as shown FIG. 5 herein. See also van Wijk et al., (2012) Mol cell 47:1-13, in which UBDs are used for the same purpose as inactive DUBs are used herein. Alternatively, it can be carried out with proteins isolated from cells, to identify proteins carrying a particular type of ubiquitination.

Moreover, DUBs which generate monoubiquitinated or multiubiquitinated species of a substrate protein can be used to facilitate identification of ubiquitination sites on proteins. Collapsing the polyubiquitin chain to a single residue allows the site of ubiquitination to be identified, whilst avoiding the complications produced by polyubiquitin in, for example, mass spectrometry.

Labelling using inactive DUBs and cleavage using active DUBs can be combined to produce a label-specific readout to detect the presence of linkages in a polyubiquitin chain being studied. For example, labelling by an inactivated, labelled DUB will be disrupted in the presence of an unlabelled, active DUB, since the linkage to which the inactivated DUB seeks to bind will be disassembled by the active DUB. Thus, inclusion of active and inactive DUBs in a reaction can provide a label-based readout of the presence or absence of particular linkages in the studies polyubiquitin polymer.

Labelling of ubiquitin chains can be detected by any suitable technique. For example, ubiquitinated proteins can be precipitated from solution, retained on an affinity matrix or otherwise washed free of unbound label, and the presence, or absence, of a label bound to the ubiquitin can be assessed.

Alternatively, interference readouts, such as FRET, can be used by combining a first label, placed for example on the protein itself, with a second label associated with the ubiquitin by means of the linkage-specific DUB. Another technique, polarisation anisotropy, relies on rotation of dye molecules and can be used with single dyes, which rotate more slowly if incorporated into a polymer.

OTULIN

Met1-/Linear linked ubiquitin chains are key players in mediating the inflammatory response through NFκB signalling and recently an E3 ligase complex (LUBAC) has been demonstrated to form linear linked poly-ubiquitin chains. However, the corresponding DUB that negatively regulates this signal has been elusive. We have identified a gene of unknown function, Fam105B, to be a DUB from the Ovarian Tumor family, which we have named OTULIN. This protein specifically hydrolyses linear linked ubiquitin chains.

Kits

Kits can be provided which facilitate the analysis of polyubiquitin chains. Such kits advantageously comprise DUB enzymes capable of disassociating two or more specific ubiquitin linkages.

Kits can also comprise packaging and instructions for use.

In one embodiment, a kit can further comprise one or more of ubiquitin and/or a mutant ubiquitin, ATP, Tris buffer (pH 7.5), $MgCl_2$ and DTT.

The components of the kit are advantageously provided in separate containers.

EXAMPLES

Methods

Cloning and Mutagenesis

OTUD3 was amplified by PCR from and cloned using the In-Fusion® system (Clontech) into the pOPIN-K vector, which incorporates a Pre-Scission protease cleavable N-terminal glutathione-S-transferase (GST) tag (Berrow et al, 2007). GST-NIeL 170-782 (pMCSG20) was a gift from David Yin-Wei Lin and Jue Chen (Lin et al, 2010). Ub mutants were generated by site-directed mutagenesis according to the QuikChange protocol but using KOD polymerase (Merck Chemicals).

Protein Production

Recombinant GST-NIeL was expressed according to (Lin et al, 2010) in Rosetta 2 (DE3) pLacI cells (Novagen) harbouring a plasmid encoding rare codons. Cultures (4-6 L) were grown in LB media to $OD_{600}$ of 0.6-0.8 and induced using 0.1 mM IPTG at 16° C. for 24 h(NIeL). All purifications were performed at 4° C. Cells were harvested and lysed by sonication in NIeL Lysis buffer (50 mM Tris [pH 8.0], 500 mM NaCl, 10% (v/v) glycerol, 1 mM EDTA, 5 mM DTT, 0.1 mg/mL DNAse I, 1 mg/mL lysozyme, Complete Mini EDTA-free protease inhibitor cocktail (Roche)). Cell lysates were cleared by centrifugation (40000 g, 30 min, 4° C.) and the supernatants incubated with Glutathione Sepharose 4B (GE Healthcare) for 1-2 h to immobilise soluble GST-tagged proteins. The beads were subsequently washed with 1 L high salt buffer (50 mM Tris pH 8.0, 500 mM NaCl, 5 mM DTT), followed by 1 L buffer A (50 mM Tris pH 8.0, 150 mM NaCl, 5 mM DTT). The GST tag was cleaved by incubation of beads with recombinant Tobacco Etch Virus (rTEV) protease overnight. Cleaved proteins were eluted and further purified by anion exchange chromatography (RESOURCE Q, GE Healthcare), applying a linear NaCl, gradient from 50-500 mM NaCl in 50 mM Tris pH 8.0, 5 mM DTT. NIeL containing fractions were finally purified by size exclusion chromatography using a Superdex75 (GE Healthcare) in buffer A. The protein was concentrated using Amicon spin concentrators (10 kDa MW cut-off) and the purity was judged by SDS-PAGE analysis to be >95%. The same protocol was applied for OTUD3 with the differences that it was expressed at 20° C. overnight and lysed in OTUD3 lysis buffer (50 mM Tris pH 8.0, 200 mM NaCl, 5 mM DTT, 1 mg/mL lysozyme, 0.1 mg/mL DNAse I). His6-tagged OTUB1 was purified according to (Edelmann et al, 2009) and the CCHFV viral OTU domain according to (Akutsu et al, 2011). Ub mutants were expressed and purified as previously described (Pickart & Raasi, 2005).

In Vitro Deubiquitination Assays

DUBs were diluted to 0.1 mg/mL (5.5 μM) for OTUD3, 0.1 mg/mL (2.7 μM) for OTUB1, 0.2 μg/mL (9.5 nM) vOTU in Dilution buffer (25 mM Tris pH 7.5, 150 mM NaCl, 10 mM DTT). Subsequently, 20 μL of diluted DUB was mixed with 4 μg polyUb and 4 μL 10×DUB buffer (500 mM Tris pH 7.5, 500 mM NaCl, 50 mM DTT) in 40 μL reactions. At given timepoints, 5 μL of the reaction was stopped by mixing with 5 μL of 4×LSD sample buffer and analysed by SDS-PAGE. Protein was visualised using silver staining using the Silver Stain Plus Kit (Bio-Rad) following the manufacturer's protocol.

Example 1

We have analysed a panel of DUBs using gel electrophoresis of products of reaction with polyubiquitin having defined linkages.

Figure 1A:
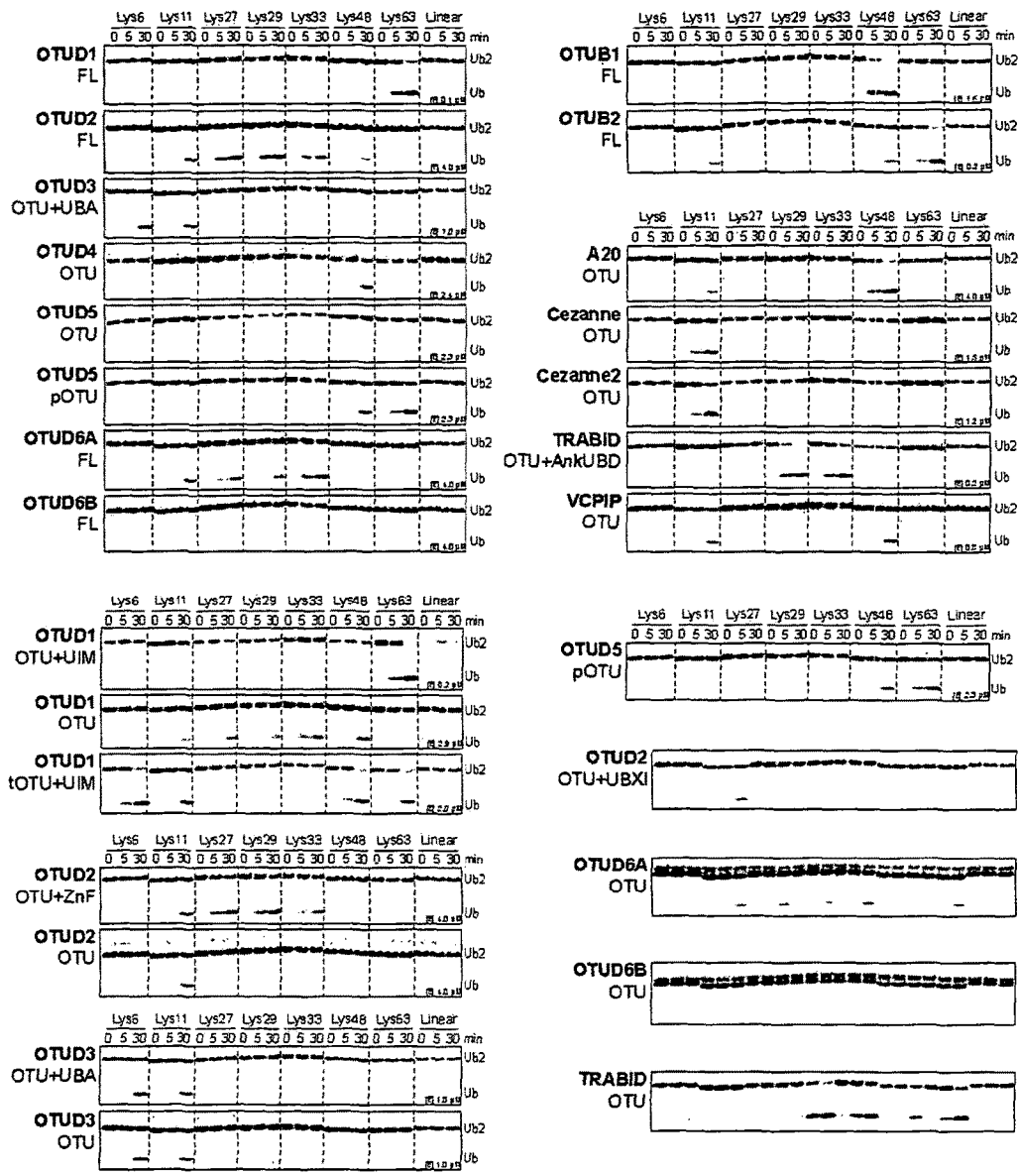
FIG. 1: Ub chain assembly by NIeL
(a) NIeL was used in Ub chain assembly reactions with E1, UBE2L3/UbcH7, and Ub mutants as indicated. M, marker; wt, wild-type Ub; Ub-Lys only mutants, Ub mutants with Arg mutations in six out of seven Lys residues; Lysless, Ub harboring Arg mutations at all Lys residues. (b) A comparison of assembled unanchored Ub chains from wt Ub, Ub K6R and Ub K48R. Ub K6R and K48R lead to the assembly of Lys48 and Lys6 chains respectively. A Ub K6R/K48R double mutant is unable to assemble similar unanchored Ub products. Asterisks (*) label pentaUb species.

As shown in FIG. 1, we have defined a panel of DUBs with specificity for each possible ubiquitin linkage.

Figure 1B:
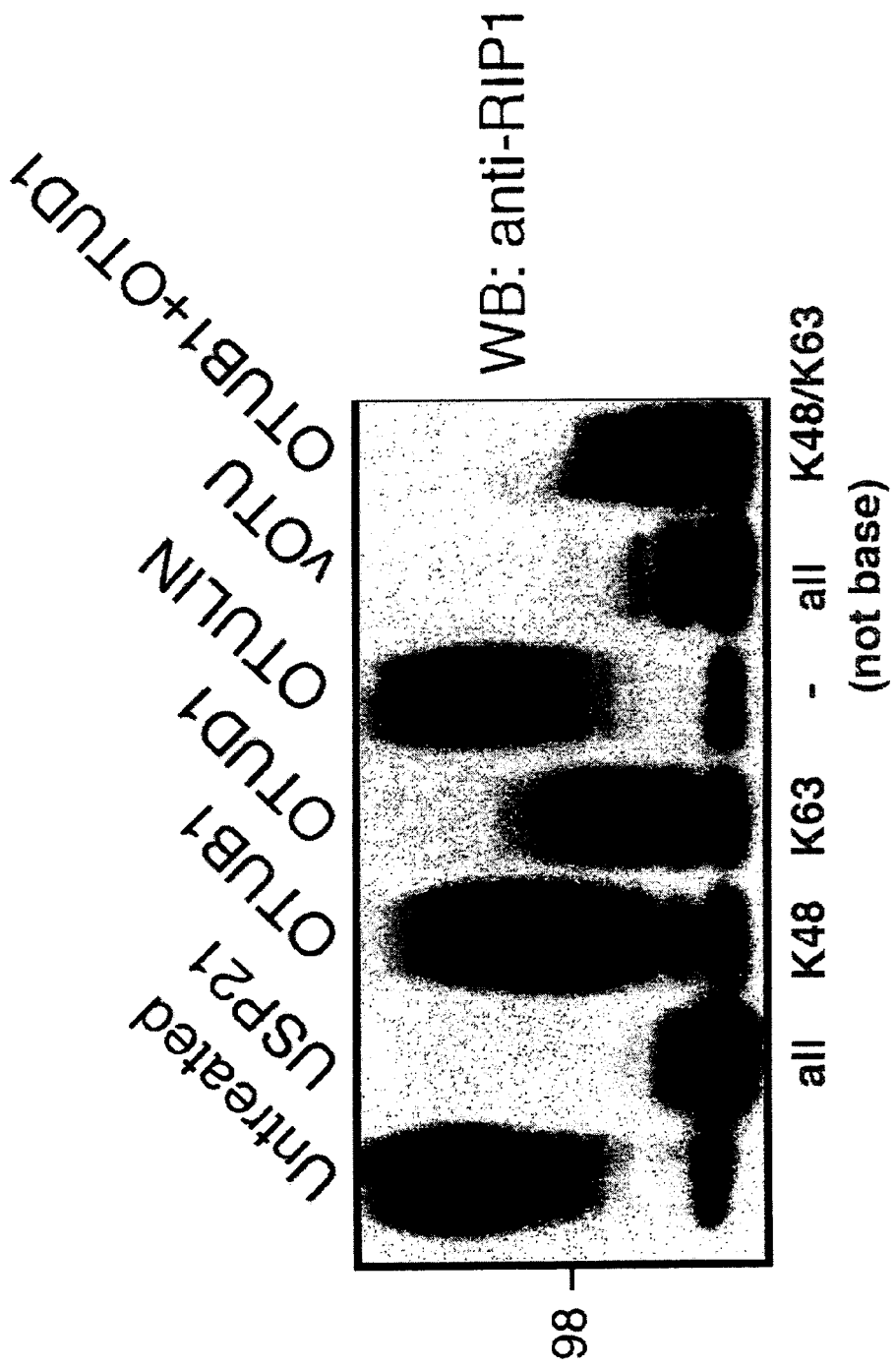

FIG. 1b shows the ubiquitin chain sequencing of polyubiquinated RIP1 using western blotting quantities of substrate. K48 and K63 linkages are identified by cleavage with OTUB1 and OTUD1. The figure shows an immunoprecipitation with the TNF-receptor, which brings down endogenously polyubiquitinted RIP1, and is detected with an anti-RIP1-antibody. The smear is as a result of ubiquitination.

RIP1 is then incubated, whilst still on the beads, with DUBs:

USP21—non-specific, can cleave all Ub from the beads

OTUB1—K48-specific, cleaves some but not many, of the Ub chains

OTUD1—K63-specific, can cleave most chains, but importantly leaves the last Ub molecules on the protein.

OTULIN—linear specific, does not change the RIP1-smear, meaning that there are not many linear linkages on the protein. See FIG. 8.

vOTU—a non-specific viral DUB that cleaves all Ub chains off RIP1, again leaving a mono-ubiquitinated species OTUB1+OTUD1—combination of a K48 and K63-specific DUB cleaves most chains.

Example 2

NIeL Assembles Heterotypic K6/K48 Chains In Vitro

Figure 2:
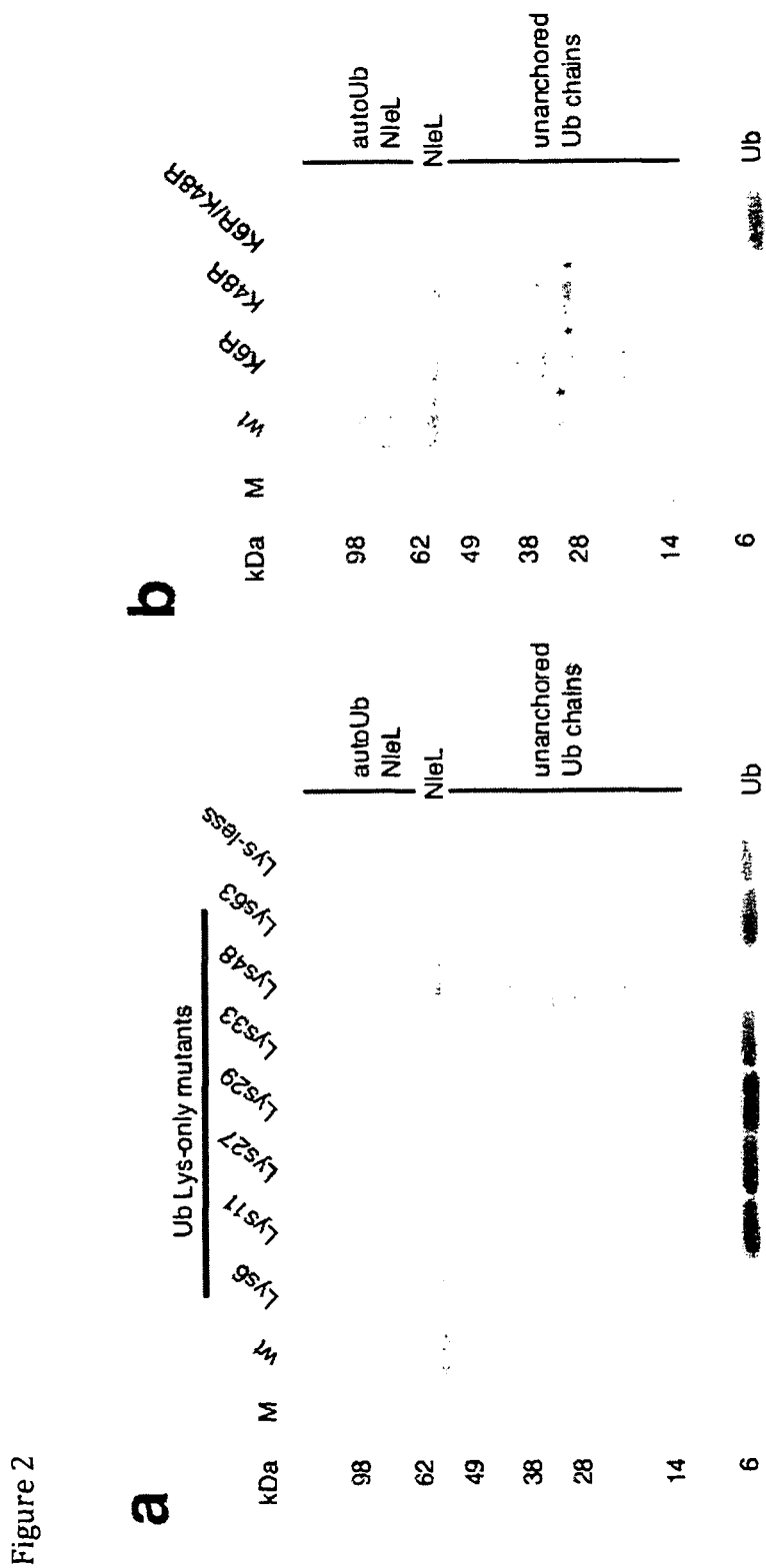
FIG. 2: Ubiquitin chain analysis
A) Schematic illustrating potential tetramer complexity in NIeL assembled wt Ub products, and the concept of Ub chain sequencing. Ub (yellow square) can be linked either via Lys6 (blue line; horizontal) or Lys48 (red line; vertical), leading to 14 distinct species (boxed). An orange dot indicates the free C-terminus of Ub (proximal moiety). Right, linkage-specific DUBs can be used as 'Ub chain restriction enzymes' to reveal building blocks within heterotypic Ub chains. B) Specificity profile of OTUB1 and OTUD3 against diUb of all Ub linkages. A time course analysis is shown where enzyme was incubated with specified diUb for a given time, then resolved by SDS-PAGE and silver stained. (D) Ubiquitin chain sequencing on western blot material, using UTUB1 and OTUD1, revealing K48 and K63 linkages in polyubiquitinated RIP1. (E) Time-course analysis of NIeL assembly reaction (as in FIG. 1a) with Ub K6R, Ub K48R and a combination of Ub ΔG76 and Ub K6R/K48R in a 1:2 molar ratio. (F) Schematic depicting the assembly of a branched triUb harboring one Lys6- and one Lys48-linkage. (G) NIeL mediated assembly of Ub chains from Ub K6 only, Ub K48 only and combination of Ub ΔG76 and Ub K6R/K48R in a 1:2 molar ratio. Resulting species are labeled.
Figure 2:
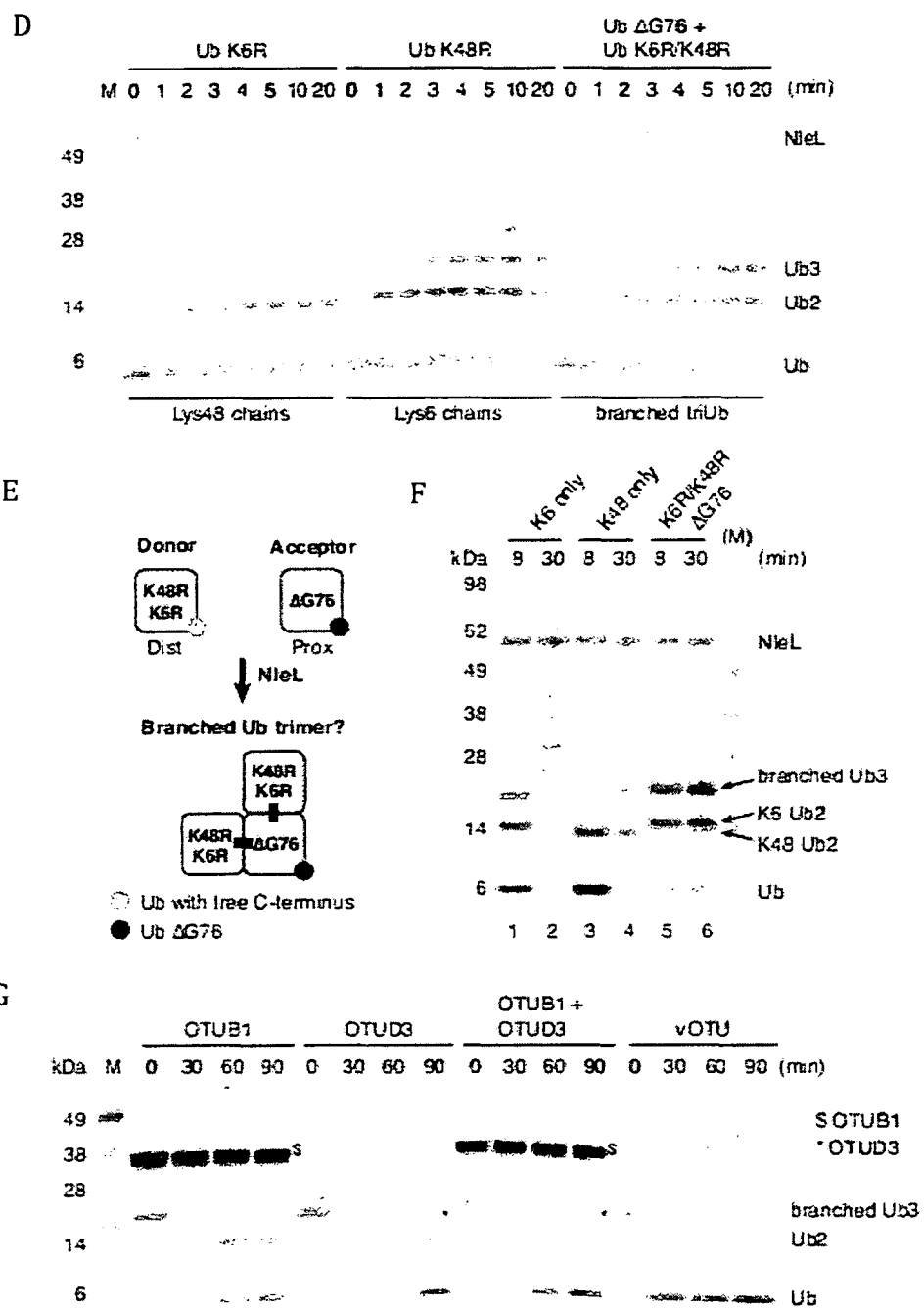

We produced NIeL in bacteria, and characterized its in vitro chain assembly capability using E1 and UBE2L3/UbcH7. NIeL assembles unanchored Ub chains with wild-type (wt) Ub, and the set of single-Lys Ub mutants showed NIeL specificity for Lys6 and Lys48 (FIG. 2a), as reported previously (Lin et al 2010). Mutation of either Ub Lys6 or Lys48 to Arg (K6R, K48R) resulted in free Ub chains of the other type, while a double mutant K6/48R was unable to assemble unanchored Ub chains efficiently (FIG. 2b).

Electrophoretic mobility of Ub chains with three or more Ub molecules varies with linkage type, which can be used diagnostically (Komander et al, 2009a0. We observed a double band for diUb assembled from wt Ub, indicating different electrophoretic mobility of Lys6 and Lys48 diUb. In longer chains (e.g. pentaUb, FIG. 2b) the electrophoretic mobility of wt polymers is different to that of both Ub point mutants, suggesting that NIeL assembles heterotypic Ub chains comprising both Lys6- and Lys48-linkages in the same polymer (FIG. 2b).

Example 3

Identification of Linkage Specific DUBs

Despite the observed K6-linkage assembly in vitro using the K48R mutant Ub, the amount and length of K6 vs. K48-linked Ub chains in NIeL conjugates with Ub was unclear. It was considered possible that K6-linkages were an insignificant by-product of the K48 ligase NIeL. However, the architecture of heterotypic Ub chains is difficult to assess by current technologies such as mass-spectroscopy (Dammer & Peng, 2010).

We therefore set out to establish biochemical approaches to assess Ub chain architecture. We reasoned that linkage-specific DUBs could serve as "Ub chain restriction enzymes", to reveal building blocks comprising distinct linkages (FIG. 3A).

Ubiquitin specific proteases (USPs) hydrolyse all types of chains, and the broad-specificity enzyme USP21 cleaved K6- and K48-linked diUb similarly (FIG. 3b); (Ye et al, 2011). In contrast, the ovarian tumour (OTU) family of DUBs comprises enzymes with marked linkage preference. An OTU enzyme with preference for K48-linkages, OTUB1, has been reported (Wang et al, 2009). Importantly, OTUB1 was unable to cleave K6-linked tetraUb under conditions where K48 linked tetraUb was fully hydrolysed (FIG. 3b—shown for diUb). This makes OTUB1 suitable to characterize heterotypic NIeL assembled Ub chains.

In contrast, the non-specific viral OTU domain (vOTU) from Crimean Congo Hemorrhagic Fever Virus (CCHFV) (Akutsu, M et al, (2011) P Natl Acad Sci Usa 108, 2228-2233) hydrolysed Lys6- and Lys48-linkages similarly.

However, an enzyme that preferred K6- to K48-linkages has not been reported. We therefore tested a panel of OTU domain DUBs for activity against K6-linked diUb, and discovered that OTUD3, an uncharacterized OTU enzyme, shows strong activity against K6-linkages, but is inefficient against K48-polymers (FIG. 3b).

Together, vOTU, OTUB1 and OTUD3 could be used to analyse Ub chain architecture of NIeL assembled Ub chains in vitro. Purified heterotypic penta/hexa Ub (FIG. 3c, lane 1) was cleaved with vOTU, revealing that vOTU can access all linkages within the mixed/branched polymers (FIG. 3c, lanes 13-15). Likewise, OTUB1 in combination with OTUD3 hydrolysed all linkages (FIG. 3c, lanes 10-12). Interestingly, OTUB1 alone disassembled heterotypic Ub chains to sharp bands corresponding to mono, di-, tri-, and tetraUb (FIG. 3c, lanes 4-6). The resulting Ub chains are K6-linked, as they show an identical electrophoretic mobility as K48 Ub chains, and can be cleaved by subsequent treatment with OTUD3.

Strikingly, when the heterogeneous penta/hexaUb input was treated with OTUD3, a different banding pattern was observed, that consisted of mainly of mono- and diUb and a faint signal for triUb (FIG. 3c, lanes 7-9). The remaining K48 chains can be easily distinguished as they show distinct electrophoretic mobility as compared to K6-linked chains (FIG. 3c, compare lane 6 and 8), and are readily cleaved upon incubation with OTUB1.

The distinct hydrolysis profile allows us to conclude that heterotypic penta/hexaUb chains assembled by NIeL (i) are heterotypic with most individual polymers comprising more than one linkage type, (ii) are primarily K6-linked and (iii) comprise rarely more than one or two K48 linkage in a row. [[quantification using SYBR RUBY missing]]. This suggests that NIeL is able to elongate K6-linked Ub chains more efficiently, while it has problems to elongate K48-linkages and stops at diUb. We are unable to distinguish between branched and mixed chains.

We also determined that our technique can sequence branched ubiquitin chains. The pattern observed for OTUD3 cleavage suggested a prevalence of Lys6-linkages in heterotypic chains. Comparison of the assembly of Ub K6R with Ub K48R into homotypic Ub chains over a short time course supported this notion (FIG. 3d). While Lys6-linkages were assembled into long polymers within minutes, assembly of Lys48-linkages was inhibited, stopping at diUb and small amounts of triUb under identical conditions (FIG. 3d). The results from Ub chain sequencing unambiguously revealed heterotypic Ub chains, but could not distinguish whether such Ub chains featured mixed or branched linkages. To test whether NIeL can assemble branched species, an assembly reaction was performed with Ub ΔG76 as the acceptor, and Ub K6R/K48R as the donor Ub (FIG. 3f). NIeL was capable of assembling branched triUb (FIG. 3d, f), showing that all forms of branched and mixed Ub chains potentially exist in NIeL products. Interestingly, Lys6-linkages are also the preferred diUb intermediate on the assembly route to branched triUb species (FIG. 3d, f). The branched triUb species could be purified and analyzed in DUB assays. DUB assays performed as for Ub chain sequencing showed that OTUD3 and OTUB1 hydrolyzed their preferred linkages identically regardless of whether the Ub chain was homotypic or branched (FIG. 3g). Similar results were obtained with DUBs from the USP family (USP7, USP21).

Example 4

Alteration of Linkage Specificity in OTU DUBs

Here, we tested the DUB activity of Trabid against the complete panel of eight different Ub linkages, and show that it cleaves Lys29- and Lys33-linkages with marked preference over Lys63-linkages, but no other chain type.

A crystal structure of the N-terminally extended Trabid OTU domain revealed a catalytic fold similar to that of A20, which is extended by two Ankyrin (Ank) repeats positioned such that they could form a proximal Ub binding site. Indeed, the isolated Ank domain binds to Ub, and NMR experiments map the interaction interfaces to a conserved hydrophobic surface of the Ank module and to the hydrophobic Ile44 patch of Ub.

We provide evidence that the Ankyrin repeat Ub binding domain (AnkUBD) contributes to enzymatic efficiency and linkage-specificity in vitro and in vivo.

Specificity of the Extended Catalytic OTU Domain of Trabid

The human Trabid protein spans 708 amino acids (aa) and comprises three N-terminal NpI4-like zinc finger (NZF) domains (aa 1-200), and a C-terminal OTU domain (aa 340-700). The C-terminal OTU domain of Trabid is closely related to the previously characterized OTU domain of A20. However, a stretch of ~100 highly conserved residues upstream of the Trabid OTU domain (aa 245-340) indicated an extension of the catalytic fold not present in A20. The extended fragment of the Trabid OTU domain (aa 245-697) was tested against the complete panel of eight differently linked diUb molecules. In this qualitative analysis, we defined DUB specificity as the enzymatic concentration at which the preferred linkage type is cleaved completely at a defined timepoint. Trabid cleaved Lys29- and Lys33-linked diUb with higher activity compared to Lys63-linkages, consistent with previous quantitative data. The remaining diUb molecules linked through Lys6, Lys11, Lys27 or Lys48, or linear diUb, were not cleaved. Hence, Trabid has a dual specificity against two atypical Ub chains linked via Lys29 and Lys33, in marked preference over Lys63-linkages.

Crystal Structure of the Extended OTU Domain Reveals Ank Repeats

To understand the molecular basis for the unique DUB specificity of Trabid, the extended OTU domain was purified to homogeneity and crystallized. Fold analysis of the α-helical domain (aa 245-340) with the Dali server revealed the presence of two Ankyrin (Ank) repeats. Ank repeats comprise ~30 aa and consist of two interacting helices connected by short loops. Multiple repeats 'stack' via a conserved Ank motif, forming arc-shaped structures. In Trabid, the first Ank repeat spans aa 260-290 and is connected to the second repeat (aa 313-340) by a long linker that packs against what would correspond to the concave surface in an extended Ank repeat structure. However, a conserved N-terminal helix (αA0, aa 245-259) that packs against the first Ank repeat, and the C-terminal OTU domain that directly extends from the second repeat, define the boundaries for the two Ank repeats in Trabid. The primary sequence of these terminal repeats is divergent from the easily identifiable Ank motif in internal repeats, explaining why the Ank domain of Trabid had not previously been annotated. NMR studies showed that the Ank domain is important for ubiquitin binding.

AnkUBD Contributes to the Binding Specificity

The presence of the AnkUBD as a Ub binding fold in close proximity to the catalytic site suggested that it may serve as an enzymatic S1' Ub binding site, directly affecting Trabid's DUB efficiency. Moreover, the S1' site may impact on Trabid specificity, as it may preferentially present a subset of Ub Lys residues to the catalytic site. Indeed, the crystallized fragment including AnkUBD and OTU domain (AnkOTU) displayed significantly higher DUB activity compared to the isolated OTU domain (OTU, aa 339-697), which was significantly less active at similar concentration and was hence used at 5-fold higher concentration to allow detection of enzymatic activity. The OTU fragment hydrolyzed Lys29, Lys33 and Lys63 with similar efficiency, but in addition also Lys48-linkages and with low efficiency Lys6- and Lys11-linked diUb. This contrasted with the AnkOTU fragment that cleaved Lys29-, Lys33- and less efficiently Lys63-linked diUb. This result was reflected in a second analysis, in which Trabid variants were purified by virtue of an N-terminal 3×FLAG-tag from HEK293 cells and used in endpoint DUB assays. Full-length (FL) Trabid, like AnkOTU, only cleaved Lys29-, Lys33- and Lys63-linked diUb over night, while an OTU construct was more promiscuous, and cleaved Lys48-linked diUb (as well as weakly Lys6- and Lys11-linkages) (FIG. 6). The specificity of HEK293 expressed Trabid variants for Lys29/Lys33-linkages was confirmed by time course analysis, in which these linkages were cleaved within 60 min by FL and AnkOTU Trabid, while Lys63-linked diUb was not cleaved during the first hour but only after overnight incubation. Together, these data show that the AnkUBD restricts activity of the OTU domain, which cleaves (at least) four linkage types, to make Trabid most efficient for Lys29 and Lys33 linkages. Removal of the AnkUBD from either construct (i.e. FL ΔAnk, and OTU), also resulted in less active protein without noticeable activity in the first 60 min, confirming the role of the AnkUBD in Trabid efficiency.

Figure 3:
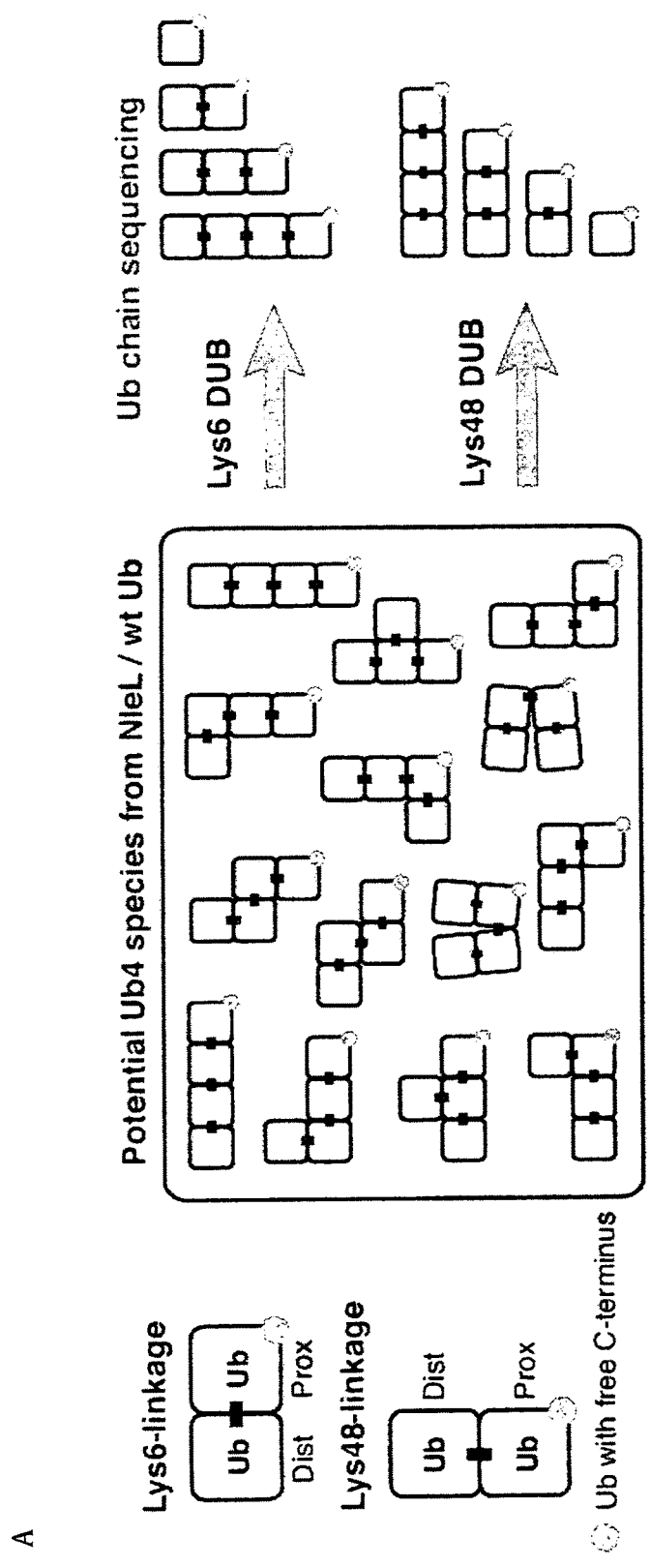
FIG. 3: Panel of linkage-specific OTU DUBs
(A) Deubiquitination assays using purified bacterial enzymes were performed as reported before (Akutsu, et al., Proc Natl Acad Sci USA 108, 2228-33 (2011)). DUBs were diluted to 2× final concentration in 150 mM NaCl, 25 mM Tris (pH 7.5) and 10 mM DTT and activated at 23° C. for 10 min. Subsequently, 10 µL of diluted enzyme were mixed with 1-2 µg diUb and 2 µL of 10×DUB buffer (500 mM NaCl, 500 mM Tris [pH 7.5] and 50 mM DTT) in a 20 µL reaction. For DUB assays, 6 µL of eluted enzyme was used in a 12 µL reaction in DUB buffer containing 200 ng diUb as indicated in the figure. Reactions were stopped by addition of 4 µL LDS sample buffer (containing 100 mM DTT) after 0, 5 or 30 min incubation at 37° C. Ub cleavage was detected by silver staining using the Silver Stain Plus kit (BioRad).
(B) An OTU DUB for every linkage; gel shows cleavage of every type of ubiquitin linkage using a DUB enzyme.
Figure 3:
Figure 3C:
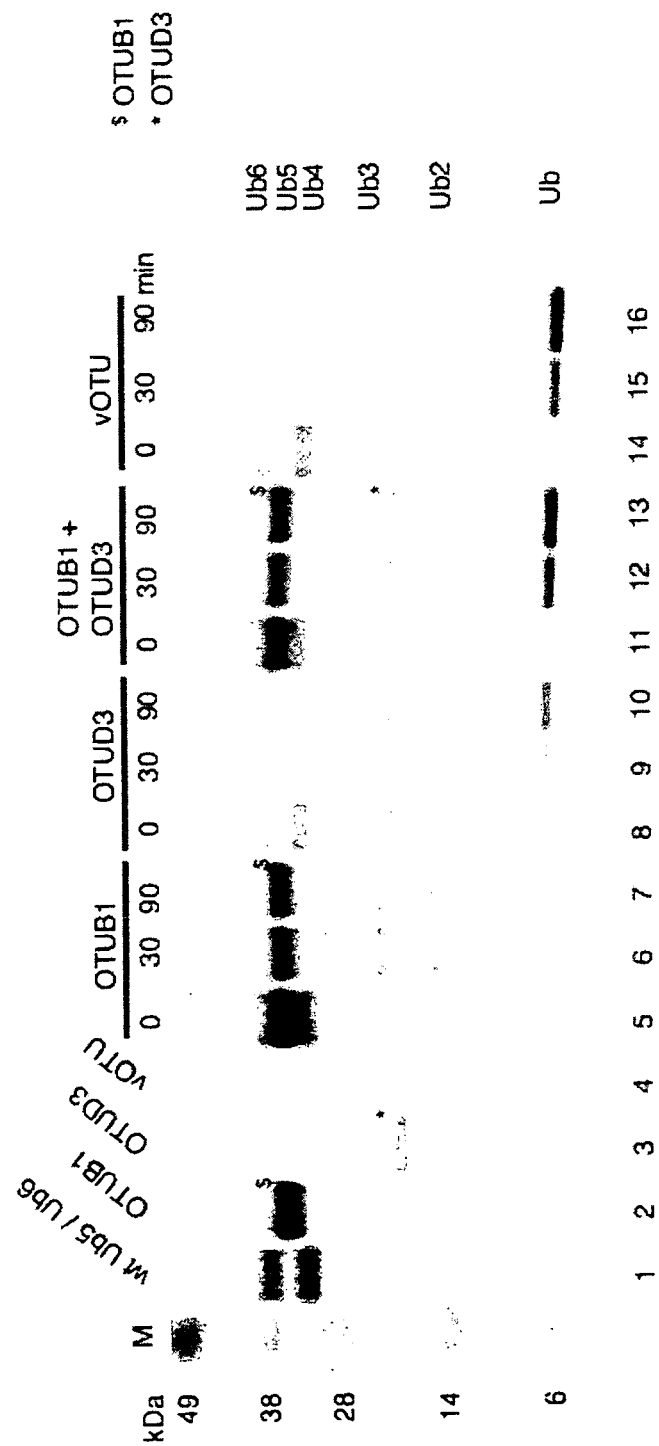

We next analyzed HEK293 expressed Trabid variants with point mutations in the AnkUBD that affect Ub binding (FIG. 3). Mutation of H317A, L332E and I320D in the AnkUBD significantly reduced Trabid activity against diUb substrates, either in context of the FL protein or in context of bacterially produced AnkOTU. The observed reduced activity of Trabid point mutants (in particular H317A, L332E) was similar to removal of the AnkUBD from either construct.

Although Lys29 and Lys33 linkages are available only as diubiquitin, Lys63-linked ubiquitin chains are available as longer polymers, so we next studied the activity of TRABID variants against Lys63-linked hexaubiquitin. Full-length TRABID cleaved hexaubiquitin efficiently, hydrolyzing most input material within 60 min. Consistent with our diubiquitin assays, removal or mutation of the AnkUBD decreased activity against K63-linked hexaubiquitin, suggesting that the AnkUBD is also essential for hydrolysis of longer polyubiquitin chains.

NZF Domains Contribute to Hydrolysis of Longer Ubiquitin Chains

TRABID contains three N-terminal NZF domains, which may also affect TRABID activity and specificity. A TRABID variant with mutations in all three NZF domains (changing the Thr-Tyr motif to Leu-Val35 for the full-length NZF mutant (FL NZFmut)) was as active against diubiquitin as full-length TRABID or AnkOTU (FIG. 5a). However full-length NZFmut TRABID was less active than full-length TRABID, when longer Lys63 chains were used as a substrate (FIG. 5b), suggesting that the NZF domains contribute to cleaving longer ubiquitin chains by providing additional binding sites. The combined S1-S1' site in TRABID may constitute the highest affinity diubiquitin-binding module (FIG. 5c), otherwise the NZF domains would compete for binding to the hydrophobic patches in diubiquitin and render TRABID less active toward diubiquitin substrates, which was not the case. The NZF domains, however, provide increased affinity for longer TRABID substrates that can bind simultaneously to AnkOTU and NZF domains (FIG. 5d).

Overall, our in vitro analysis showed that (i) the TRABID OTU domain cleaves four out of eight linkage types, (ii) addition of the AnkUBD increases activity of TRABID for Lys29 and Lys33 linkages, effectively making it specific for these linkages (FIG. 5c) and (iii) the N-terminal NZF domain does not affect TRABID specificity against diubiquitin but may increase the efficiency of the enzyme against longer polymers (FIG. 5d). This confirms the importance of the AnkUBD as a crucial determinant of TRABID DUB efficiency and specificity in vitro.

Inactive TRABID Forms Puncta Enriched in Atypical Polyubiquitin

We next set out to provide evidence for the mechanistic models shown in FIG. 5c, d in a physiological setting, for which we had to establish DUB assays in vivo. It has been reported that hemagglutinin (HA)-tagged, catalytically inactive, full-length TRABID C443S (that is, mutation of the catalytic Cys443 to serine) forms distinct cytoplasmic puncta upon overexpression in various human cell lines, whereas wild-type (WT) TRABID is distributed diffusely throughout the cytoplasm and nucleus35. An equivalent localization was observed with green fluorescent protein (GFP)-tagged TRABID, for full-length WT and full-length C443S (FIG. 5e, f). We used the latter for fluorescence recovery after photobleaching (FRAP) experiments, revealing that the full-length C443S puncta are highly dynamic (that is, 50% of puncta fluorescence recovers within 30 s) and in rapid equilibrium exchange with the diffuse protein. Thus, inactive TRABID forms dynamic protein assemblies rather than stable aggregates.

Example 5

Modification of OTU Domain Specificity

The presence of the AnkUBD as a ubiquitin-binding fold in close proximity to the catalytic site suggests that it may serve as an enzymatic S1' ubiquitin-binding site, directly affecting TRABID's DUB efficiency. Moreover, the S1' site may affect TRABID specificity, as it may preferentially present a subset of ubiquitin lysine residues to the catalytic site. Indeed, the crystallized fragment that included the AnkUBD and the AnkOTU domain showed higher DUB activity compared to the isolated OTU domain (residues 339-697), which was less active at similar concentration. The concentration of the isolated OTU domain was thus increased by six-fold to allow us to detect enzymatic activity (FIG. 6a). The OTU fragment hydrolyzed Lys29, Lys33 and Lys63 with similar efficiency and also hydrolyzed Lys48 linkages. In addition, Lys6- and Lys11-linked diubiquitin was also cleaved but with low efficiency (FIG. 6a). This contrasted with the AnkOTU fragment, which cleaved Lys29-linked and Lys33-linked ubiquitin and—less efficiently—Lys63-linked diubiquitin (FIG. 6a).

This result was reflected in a second analysis, in which TRABID variants were purified by using an N-terminal 3× Flag-tag from HEK293 cells and used in endpoint DUB assays. Full-length TRABID, similarly to AnkOTU, only cleaved Lys29-, Lys33- and Lys63-linked diubiquitin when left overnight for 16 h, whereas an OTU construct was more promiscuous, cleaving Lys48-linked diubiquitin (as well as weakly cleaving Lys6 and Lys11 linkages) (FIG. 6b). We confirmed the specificity of HEK293-expressed TRABID variants for Lys29 and Lys33 linkages by time-course analysis, in which these linkages were cleaved within 60 min by full-length and AnkOTU TRABID, whereas Lys63-linked diubiquitin was not cleaved during the first hour but only after incubation overnight for 16 h (FIG. 6c, panels 1 and 3 from the top). Although this was not a quantitative analysis, there was slightly higher activity of TRABID against Lys29 linkages compared to Lys33 linkages in our qualitative time-course assays (FIG. 6a,c). Together, these data show that the AnkUBD restricts activity of the OTU domain, which cleaves (at least) four linkage types, to make TRABID most efficient for hydrolyzing Lys29 and Lys33 linkages.

Removal of the AnkUBD from either construct (that is, from full-length ΔAnk (FL ΔAnk) or OTU) also resulted in a less active protein that lacked noticeable activity in the first 60 min (FIG. 6c, panels 2 and 4 from the top), confirming the role of the AnkUBD in TRABID efficiency.

We next analyzed HEK293-expressed TRABID variants with point mutations in the AnkUBD that affect ubiquitin binding. Mutation of H317A, L332E and I320D in the AnkUBD reduced TRABID activity against diubiquitin substrates, either in the context of the full-length protein (FIG. 6d) or in context of bacterially produced AnkOTU. The observed reduced activity of TRABID point mutants (in particular H317A and L332E) was similar to that resulting from removal of the AnkUBD from either construct.

Although Lys29 and Lys33 linkages are available only as diubiquitin, Lys63-linked ubiquitin chains are available as longer polymers, so we next studied the activity of TRABID variants against Lys63-linked hexaubiquitin (FIG. 6e). Full-length TRABID cleaved hexaubiquitin efficiently, hydrolyzing most input material within 60 min. Consistent with our diubiquitin assays, removal or mutation of the AnkUBD decreased activity against K63-linked hexaubiquitin (FIG. 6e), suggesting that the AnkUBD is also essential for hydrolysis of longer polyubiquitin chains.

We have moreover observed that certain OTU domains, such as the YOD1 catalytic (OTU) domain, are highly specific for a given linkage type, K11 in the case of YOD1. Others, such as the OTUD3 OTU domain, show a broader specificity, encompassing K6, K11 and K63 in the case of OTUD3.

Structural analysis of YOD1 and OTUD3 shows that the S1' site in both enzymes, which interacts with the ubiquitin peptide, is highly conserved, being the most conserved region in the two molecules. We therefore mutated the S1' site in YOD1, which has the sequence TRTV, to match the sequence in OTUD3, KLRE.

Analysis of the linkage specificity of the altered YOD1 showed that its specificity has been extended to disassemble K6 and K48 linkages, in addition to K11 linkages (FIG. 7).

Therefore, modification of S1' sites in OTU domains can alter the specificity of the domain.

REFERENCES

Acconcia F, Sigismund S, Polo S (2009) Ubiquitin in trafficking: the network at work. *Exp Cell Res*315: 1610-1618

Akutsu M, Ye Y, Virdee S, Chin J W, Komander D (2011) Molecular basis for ubiquitin and ISG15 cross-reactivity in viral ovarian tumor domains. *Proc Natl Acad Sci USA* 108: 2228-2233

Al-Hakim A, Escribano-Diaz C, Landry M C, O'Donnell L, Panier S, Szilard R K, Durocher D (2010) The ubiquitous role of ubiquitin in the DNA damage response. *DNA Repair* 9: 1229-1240

Bang D, Gribenko A V, Tereshko V, Kossiakoff A A, Kent S B, Makhatadze G I (2006) Dissecting the energetics of protein alpha-helix C-cap termination through chemical protein synthesis. *Nat Chem Biol* 2: 139-143

Ben-Saadon R, Zaaroor D, Ziv T, Ciechanover A (2006) The polycomb protein Ring1B generates self atypical mixed ubiquitin chains required for its in vitro histone H2A ligase activity. *Mol Cell* 24: 701-711

Berrow N S, Alderton D, Sainsbury S, Nettleship J, Assenberg R, Rahman N, Stuart D I, Owens R J (2007) A versatile ligation-independent cloning method suitable for high-throughput expression screening applications. *Nucleic Acids Res* 35: e45

Bremm A, Komander D (2011) Emerging roles for Lys11-linked polyubiquitin in cellular regulation. *Trends Biochem Sci* 36: 355-363

Chen Z J, Sun L J (2009) Nonproteolytic functions of ubiquitin in cell signaling. *Mol Cell* 33: 275-286

Dammer E, Peng J (2010) At the crossroads of ubiquitin signaling and mass spectrometry. *Expert review of proteomics* 7: 643-645

Dammer E B, Na C H, Xu P, Seyfried N T, Duong D M, Cheng D, Gearing M, Rees H, Lah J J, Levey A I, Rush J, Peng J (2011) Polyubiquitin linkage profiles in three models of proteolytic stress suggest the etiology of Alzheimer disease. *J Biol Chem* 286: 10457-10465

Datta A B, Hura G L, Wolberger C (2009) The structure and conformation of Lys63-linked tetraubiquitin. *J Mol Biol* 392: 1117-1124

Deshaies R J, Joazeiro C A (2009) RING domain E3 ubiquitin ligases. *Annu Rev Biochem* 78: 399-434

Dikic I, Wakatsuki S, Walters K J (2009) Ubiquitin-binding domains—from structures to functions. *Nat Rev Mol Cell Biol* 10: 659-671

Dye B T, Schulman B A (2007) Structural mechanisms underlying posttranslational modification by ubiquitin-like proteins. *Annu Rev Biophys Biomol Struct* 36: 131-150

Edelmann M J, Iphofer A, Akutsu M, Altun M, di Gleria K, Kramer H B, Fiebiger E, Dhe-Paganon S, Kessler B M (2009) Structural basis and specificity of human otubain 1-mediated deubiquitination. *Biochem J* 418: 379-390

Hershko A, Ciechanover A (1998) The ubiquitin system. *Annu Rev Biochem* 67: 425-479

Iwai K, Tokunaga F (2009) Linear polyubiquitination: a new regulator of NF-kappaB activation. *EMBO Rep* 10: 706-713

Komander D (2009) The emerging complexity of protein ubiquitination. *Biochem Soc Trans* 37: 937-953

Komander D, Clague M J, Urbé S (2009a) Breaking the chains: structure and function of the deubiquitinases. *Nat Rev Mol Cell Biol* 10: 550-563

Komander D, Reyes-Turcu F, Licchesi J D, Odenwaelder P, Wilkinson K D, Barford D (2009b) Molecular discrimination of structurally equivalent Lys 63-linked and linear polyubiquitin chains. *EMBO Rep* 10: 466-473

Lange O F, Lakomek N-A, Fares C, Schroder G F, Walter K F A, Becker S, Meiler J, Grubmüller H, Griesinger C, de Groot B L (2008) Recognition dynamics up to microseconds revealed from an RDC-derived ubiquitin ensemble in solution. *Science* 320: 1471-1475

Lin D Y, Diao J, Zhou D, Chen J (2011) Biochemical and structural studies of a HECT-like ubiquitin ligase from *E. coli* O157:H7. *J Biol Chem* 286:441-49

Morris J R, Solomon E (2004) BRCA1: BARD1 induces the formation of conjugated ubiquitin structures, dependent on K6 of ubiquitin, in cells during DNA replication and repair. *Hum Mol Genet* 13: 807-817

Nishikawa H, Ooka S, Sato K, Arima K, Okamoto J, Klevit R E, Fukuda M, Ohta T (2004) Mass spectrometric and mutational analyses reveal Lys-6-linked polyubiquitin chains catalyzed by BRCA1-BARD1 ubiquitin ligase. *J Biol Chem* 279: 3916-3924

Pickart C M, Raasi S (2005) Controlled synthesis of polyubiquitin chains. *Methods Enzymol* 399: 21-36

Piscatelli H, Kotkar S A, McBee M E, Muthupalani S, Schauer D B, Mandrell R E, Leong J M, Zhou D (2011) The EHEC type III effector NleL is an E3 ubiquitin ligase that modulates pedestal formation. *PloS one* 6: e19331

Randow F, Lehner P J (2009) Viral avoidance and exploitation of the ubiquitin system. *Nat Cell Biol* 11: 527-534

Reyes-Turcu F E, Ventii K H, Wilkinson K D (2009) Regulation and cellular roles of ubiquitin-specific deubiquitinating enzymes. *Annu Rev Biochem* 78: 363-397

Rotin D, Kumar S (2009) Physiological functions of the HECT family of ubiquitin ligases. *Nat Rev Mol Cell Biol* 10: 398-409

Virdee S, Ye Y, Nguyen D P, Komander D, Chin J W (2010) Engineered diubiquitin synthesis reveals Lys29-isopeptide specificity of an OTU deubiquitinase. *Nat Chem Biol* 6: 750-757

Wang T, Yin L, Cooper E M, Lai M Y, Dickey S, Pickart C M, Fushman D, Wilkinson K D, Cohen R E, Wolberger C (2009) Evidence for bidentate substrate binding as the basis for the K48 linkage specificity of otubain 1. *J Mol Biol* 386: 1011-1023

Wenzel D M, Lissounov A, Brzovic P S, Klevit R E (2011) UBCH7 reactivity profile reveals parkin and HHARI to be RING/HECT hybrids. *Nature* 474: 105-108

Wu-Baer F, Lagrazon K, Yuan W, Baer R (2003) The BRCA1/BARD1 heterodimer assembles polyubiquitin chains through an unconventional linkage involving lysine residue K6 of ubiquitin. *J Biol Chem* 278: 34743-34746

Xu P, Duong D M, Seyfried N T, Cheng D, Xie Y, Robert J, Rush J, Hochstrasser M, Finley D, Peng J (2009) Quantitative proteomics reveals the function of unconventional ubiquitin chains in proteasomal degradation. *Cell* 137: 133-145

Ye Y, Akutsu M, Reyes-Turcu F, Enchev R I, Wilkinson K D, Komander D (2011) Polyubiquitin binding and cross-reactivity in the USP domain deubiquitinase USP21. *EMBO Rep* 12: 350-357

Unless otherwise stated, all technical and scientific terms used herein have the same meanings as commonly understood by one of ordinary skill in the art to which this invention belongs. Any methods and materials similar or equivalent to those described herein can be used in the practice or testing of the present invention. Methods, devices, and materials suitable for such uses are described above. All publications cited herein are incorporated herein by reference in their entirety for the purpose of describing and disclosing the methodologies, reagents, and tools reported in the publications that might be used in connection with the invention.

The invention claimed is:

1. A method for determining a presence or absence of a linkage type in a polyubiquitin chain, comprising the steps of:
   (a) contacting an ubiquitin polymer of unknown linkage type with a first linkage-specific deubiquitinase under conditions in which the enzyme catalyses the disassociation of one or more, but less than seven, ubiquitin linkages;
   (b) analysing the product of the catalysis for the presence of lower molecular weight fractions of the ubiquitin polymer;
   (c) repeating steps (a) and (b) in the presence of a second, different linkage-specific deubiquitinase; and
   (d) identifying the presence or absence of a linkage type cleaved by the first or second deubiquitinase by the presence or absence of lower molecular weight fractions of the ubiquitin polymer in the analysis of step (b).

2. The method according to claim 1, wherein at least one of the first and second deubiquitinase is an ovarian tumour protease (OTU) family deubiquitinase (DUB).

3. The method according to claim 1, wherein the deubiquitinase catalyses the dissociation of three, two or one linkage types.

4. The method according to claim 1, wherein the product of the catalysis reaction is analysed by gel electrophoresis.

5. The method according to claim 1, wherein the lower molecular weight fractions comprise ubiquitin monomers and/or polymers.

6. The method according to claim 1, wherein the second linkage-specific deubiquitinase has a linkage specificity which overlaps with that of the first linkage-specific deubiquitinase.

7. The method according to claim 1, wherein the second linkage-specific deubiquitinase has a linkage specificity which does not overlap with that of the first linkage-specific deubiquitinase.

8. The method according to claim 2, wherein ovarian tumour protease family deubiquitinase 1 (OTUD1) is used to cleave K63 linkages.

9. The method according to claim 2, wherein ovarian tumour protease family deubiquitinase 4 (OTUD4) is used to cleave K48 linkages.

10. The method according to claim 2, wherein ovarian tumour protease family deubiquitinase 3 (OTUD3) is used to cleave K6 and/or K11 linkages.

11. The method of claim 2, wherein at least one of the first and second linkage-specific deubiquitinase has altered linkage specificity resulting from (a) addition or deletion of a UBD, or (b) mutation of the OTU S1' site.

* * * * *